United States Patent [19]
Eggers et al.

[11] Patent Number: 6,047,700
[45] Date of Patent: Apr. 11, 2000

[54] SYSTEMS AND METHODS FOR ELECTROSURGICAL REMOVAL OF CALCIFIED DEPOSITS

[75] Inventors: Philip E. Eggers, Dublin, Ohio; Hira V. Thapliyal, Los Altos, Calif.; Michael W. Jopling, Columbus, Ohio

[73] Assignee: ArthroCare Corporation, Sunnyvale, Calif.

[21] Appl. No.: 09/083,533

[22] Filed: May 22, 1998

Related U.S. Application Data

[60] Provisional application No. 60/079,922, Mar. 30, 1998.

[51] Int. Cl.[7] .................................................. A61B 19/00
[52] U.S. Cl. .............................................. 128/898; 606/41
[58] Field of Search ........................... 606/41, 42, 45–50; 607/101–105, 122; 600/374; 128/898

[56] References Cited

U.S. PATENT DOCUMENTS

| | | |
|---|---|---|
| 3,460,539 | 8/1969 | Anhalt . |
| 4,011,872 | 3/1977 | Komiya . |

(List continued on next page.)

FOREIGN PATENT DOCUMENTS

| | | |
|---|---|---|
| 0703461 | 3/1996 | European Pat. Off. . |
| 0740926 | 11/1996 | European Pat. Off. . |
| 0754437 | 1/1997 | European Pat. Off. . |
| 0812575 | 12/1997 | European Pat. Off. . |
| 57-117843 | 7/1982 | Japan . |
| 2308979 | 7/1997 | United Kingdom . |
| 2308980 | 7/1997 | United Kingdom . |
| 2308981 | 7/1997 | United Kingdom . |
| 2327350 | 1/1999 | United Kingdom . |
| 2327351 | 1/1999 | United Kingdom . |
| 2327352 | 1/1999 | United Kingdom . |
| WO 90/07303 | 7/1990 | WIPO . |
| WO 92/21278 | 12/1992 | WIPO . |
| 93/20747 | 10/1993 | WIPO . |
| 94/26228 | 11/1994 | WIPO . |
| 95/34259 | 12/1995 | WIPO . |
| 97/00646 | 1/1997 | WIPO . |
| 97/00647 | 1/1997 | WIPO . |
| 97/24073 | 7/1997 | WIPO . |
| 97/24993 | 7/1997 | WIPO . |
| 97/24994 | 7/1997 | WIPO . |
| 97/48346 | 12/1997 | WIPO . |
| 99/00060 | 1/1999 | WIPO . |

OTHER PUBLICATIONS

C. Slager et al. (1987) *Z. Kardiologie* 76(6):67–71.
C. Slager et al. (1985) *JACC* 5(6):1382–6.
P. Nardella (1989) *SPIE* 1068:42–49.
Elsasser et al. (1976) *Medizinal–Markt/Acta Medicotechnica* 24 (4) :129–134.
E. Kramolowsky et al. (1991) *J. of Urology* 146:669–674.
R. Tucker et al. (1990) *Urol. Res.* 18:291–294.
R. Tucker et al. (1989) *J. of Urology* 141:662–665.
R. Tucker et al. (1989) Abstract P14–11, 7th World Congress on Endourology and ESWL, Nov. 27–30, 1989, Kyoto, Japan.
Rand et al. (1985) *J. Arthro. Surg.* 1:242–246.
L. Salter (1996) *Catheterization and Cardiovascular Diagnosis* 37:320–321.
Topaz et al. (1996) *Catheterization and Cardiovascular Diagnosis* 37:293–299.

*Primary Examiner*—Michael Peffley
*Attorney, Agent, or Firm*—John T. Raffle

[57] ABSTRACT

The present invention provides systems and methods for selectively applying electrical energy to a target location within a patient's heart to remove calcified deposits and fibroid material from valve leaflets. The method of the present invention comprises positioning an electrosurgical probe or catheter adjacent the target site so that one or more electrode terminal(s) are brought into at least partial contact or close proximity with the target heart valve. High frequency voltage is then applied between the electrode terminal(s) and one or more return electrode(s) to volumetrically remove or ablate at least a portion of the calcified material while minimizing damage to the heart valve and substantially preserving the elastic fiber layer of the valve leaflets.

25 Claims, 25 Drawing Sheets

U.S. PATENT DOCUMENTS

| | | |
|---|---|---|
| 4,033,351 | 7/1977 | Hetzel . |
| 4,040,426 | 8/1977 | Morrison, Jr. . |
| 4,043,342 | 8/1977 | Morrison, Jr. . |
| 4,116,198 | 9/1978 | Roos . |
| 4,202,337 | 5/1980 | Hren et al. . |
| 4,228,800 | 10/1980 | Degler, Jr. et al. . |
| 4,232,676 | 11/1980 | Herczog . |
| 4,248,231 | 2/1981 | Herczog et al. . |
| 4,326,529 | 4/1982 | Doss et al. . |
| 4,381,007 | 4/1983 | Doss . |
| 4,476,862 | 10/1984 | Pao . |
| 4,532,924 | 8/1985 | Auth et al. . |
| 4,548,207 | 10/1985 | Reimels . |
| 4,567,890 | 2/1986 | Ohta et al. . |
| 4,674,499 | 6/1987 | Pao . |
| 4,682,596 | 7/1987 | Bales et al. . |
| 4,706,667 | 11/1987 | Roos . |
| 4,709,698 | 12/1987 | Johnston et al. . |
| 4,765,331 | 8/1988 | Petruzzi et al. . |
| 4,823,791 | 4/1989 | D'Amelio . |
| 4,955,377 | 9/1990 | Lennox et al. . |
| 4,967,765 | 11/1990 | Turner et al. . |
| 4,976,711 | 12/1990 | Parins et al. . |
| 4,998,933 | 3/1991 | Eggers et al. . |
| 5,007,908 | 4/1991 | Rydell . |
| 5,009,656 | 4/1991 | Reimels . |
| 5,057,105 | 10/1991 | Malone et al. . |
| 5,078,717 | 1/1992 | Parins et al. . |
| 5,078,736 | 1/1992 | Behl . |
| 5,083,565 | 1/1992 | Parins . |
| 5,098,431 | 3/1992 | Rydell . |
| 5,108,391 | 4/1992 | Flachenecker et al. . |
| 5,122,138 | 6/1992 | Manwaring . |
| 5,125,928 | 6/1992 | Parins et al. . |
| 5,178,620 | 1/1993 | Eggers et al. . |
| 5,190,517 | 3/1993 | Zieve et al. . |
| 5,195,959 | 3/1993 | Smith . |
| 5,197,963 | 3/1993 | Parins . |
| 5,217,457 | 6/1993 | Delahuerga et al. . |
| 5,222,938 | 6/1993 | Behl . |
| 5,246,438 | 9/1993 | Langberg . |
| 5,267,994 | 12/1993 | Gentelia et al. . |
| 5,267,997 | 12/1993 | Farin et al. . |
| 5,273,524 | 12/1993 | Fox et al. . |
| 5,281,216 | 1/1994 | Klicek . |
| 5,281,218 | 1/1994 | Imran . |
| 5,300,069 | 4/1994 | Hunsberger et al. . |
| 5,312,400 | 5/1994 | Bales et al. . |
| 5,314,406 | 5/1994 | Arias et al. . |
| 5,330,470 | 7/1994 | Hagen . |
| 5,336,443 | 8/1994 | Eggers et al. . |
| 5,342,357 | 8/1994 | Nardella . |
| 5,348,554 | 9/1994 | Imran et al. ............... 606/41 |
| 5,370,675 | 12/1994 | Edwards et al. . |
| 5,380,277 | 1/1995 | Phillips . |
| 5,383,917 | 1/1995 | Desai et al. . |
| 5,395,312 | 3/1995 | Desai . |
| 5,417,687 | 5/1995 | Nardella et al. . |
| 5,419,767 | 5/1995 | Eggers et al. . |
| 5,423,882 | 6/1995 | Jackman et al. ......... 607/122 |
| 5,429,604 | 7/1995 | Hammersmark et al. . |
| 5,431,649 | 7/1995 | Mulier et al. ............... 606/41 |
| 5,433,708 | 7/1995 | Nichols et al. . |
| 5,454,809 | 10/1995 | Janssen . |
| 5,514,130 | 5/1996 | Baker . |
| 5,542,928 | 8/1996 | Evans et al. . |
| 5,545,161 | 8/1996 | Imran . |
| 5,555,883 | 9/1996 | Avitall ...................... 600/374 |
| 5,556,397 | 9/1996 | Long et al. . |
| 5,569,242 | 10/1996 | Lax et al. . |
| 5,579,764 | 12/1996 | Goldreyer . |
| 5,584,872 | 12/1996 | LaFontaine et al. . |
| 5,609,151 | 3/1997 | Mulier et al. . |
| 5,643,255 | 7/1997 | Organ . |
| 5,647,869 | 7/1997 | Goble . |
| 5,673,695 | 10/1997 | McGee et al. . |
| 5,676,693 | 10/1997 | LaFontaine . |
| 5,681,282 | 10/1997 | Eggers et al. . |
| 5,683,366 | 11/1997 | Eggers et al. . |
| 5,697,281 | 12/1997 | Eggers et al. . |
| 5,697,536 | 12/1997 | Eggers et al. . |
| 5,697,882 | 12/1997 | Eggers et al. . |
| 5,697,909 | 12/1997 | Eggers et al. . |
| 5,700,262 | 12/1997 | Acosta . |
| 5,718,701 | 2/1998 | Shai et al. ................. 606/41 |
| 5,722,975 | 3/1998 | Edwards et al. ......... 606/34 |
| 5,725,524 | 3/1998 | Mulier et al. . |
| 5,766,153 | 6/1998 | Eggers et al. . |
| 5,775,338 | 7/1998 | Hastings . |
| 5,807,395 | 9/1998 | Mulier et al. . |
| 5,823,955 | 10/1998 | Kuck et al. . |
| 5,840,059 | 11/1998 | March et al. . |
| 5,860,951 | 1/1999 | Eggers et al. . |
| 5,860,974 | 1/1999 | Abele . |
| 5,873,855 | 2/1999 | Eggers et al. . |
| 5,885,277 | 3/1999 | Korth . |
| 5,897,553 | 4/1999 | Mulier et al. . |
| 5,928,224 | 7/1999 | Laufer ...................... 606/27 |
| 5,944,715 | 8/1999 | Goble et al. . |

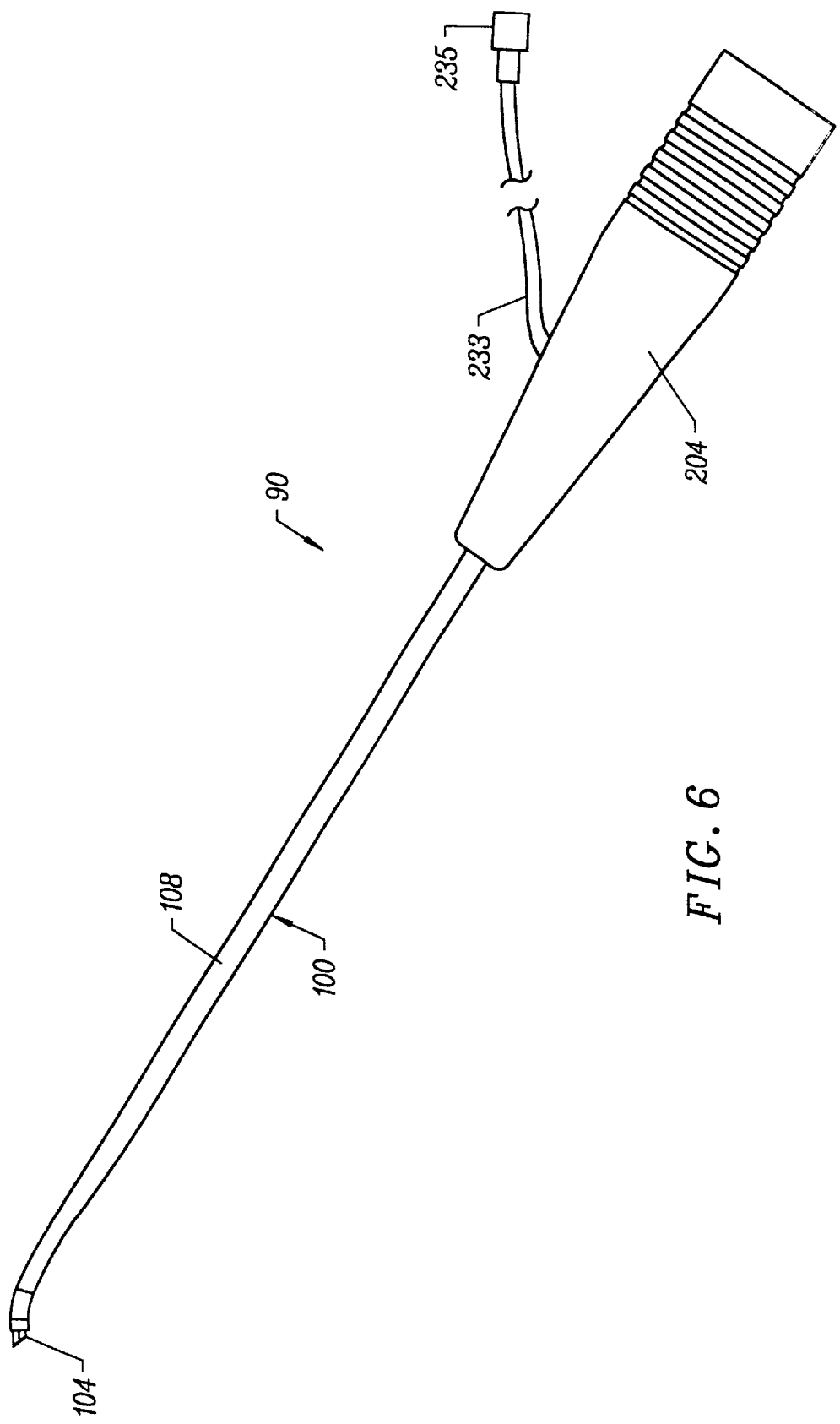

SYSTEMS AND METHODS FOR ELECTROSURGICAL REMOVAL OF CALCIFIED DEPOSITS

RELATED APPLICATIONS

The present application is a continuation-in-part of Provisional Patent Application Ser. No. 60/079,922, filed on Mar. 30, 1998, the complete disclosure of which is incorporated herein by reference for all purposes.

The present invention is related to commonly assigned co-pending U.S. patent application. No. 08/990,374, filed Dec. 15, 1997, which is a continuation-in-part of U.S. patent application. No. 08/485,219, filed on Jun. 7, 1995, now U.S. Pat. No. 5,697,281, patent application. Nos. 09/058,571, 08/874,173 and 09/002,315, filed on Apr. 10, 1998, Jun. 13, 1997, and Jan. 2, 1998, respectively and U.S. patent application. No. 09/054,323, filed on Apr. 2, 1998, U.S. patent application. No. 09/010,382, filed Jan. 21, 1998, and U.S. patent application. No. 09/032,375, filed Feb. 27, 1998, U.S. patent application. No. 08/977,845, filed on Nov. 25, 1997, Ser. No. 08/942,580, filed on Oct. 2, 1997, Ser. No. 09/026,851, filed Feb. 20, 1998, U.S. application. No. 08/753,227, filed on Nov. 22, 1996, now U.S. Pat. No. 5,873,855, U.S. application Ser. No. 08/687792, filed on Jul. 18, 1996, now U.S. Pat. No. 5,843,019, and PCT International Application, U.S. National Phase. No. PCT/US94/05168, filed on May 10, 1994, now U.S. Pat. No. 5,697,909, which was a continuation-in-part of U.S. patent application No. 08/059,681, filed on May 10, 1993 (now abandoned), which was a continuation-in-part of U.S. patent application Ser. No. 07/958,977, filed on Oct. 9, 1992, now U.S. Pat. No. 5,366,443, which was a continuation-in-part of U.S. patent application. No. 07/817,575, filed on Jan. 7, 1992 (now abandoned), the complete disclosures of which are incorporated herein by reference for all purposes. The present invention is also related to commonly assigned U.S. Pat. No. 5,683,366, filed Nov. 22, 1995, the complete disclosure of which is incorporated herein by reference for all purposes.

BACKGROUND OF THE INVENTION

The present invention relates generally to the field of electrosurgery, and more particularly to surgical devices and methods which employ high frequency electrical energy to treat tissue in regions of the heart, particularly the leaflets on various heart valves. The present invention is particularly suited for removing calcified deposits and fibroid tissue from valve leaflets and the treatment of aortic stenosis.

Recently there has been growing interest in the repair of diseased native heart valves as an alternative to prosthetic valve replacement. With operative mortality between about 5% and 12% (higher among the elderly), the risk associated with valve replacement is significant. In addition, a patient receiving a replacement valve typically must take anticoagulation drugs for the rest of his or her life. Not all patients are capable of doing this. Moreover, some patients have an aortic root that is not large enough to easily accommodate conventional replacement valves. Thus, there are a significant number of patients for whom valve replacement is either impossible, impractical, or undesirable. Preservation of native tissue by valve repair is a preferable modality to valve replacement due to imperfections in most valve substitutes, and the potential complications resulting from these prostheses, including thromboembolic events, bleeding associated with anticoagulation, bacterial endocarditis, valve thrombosis, valvular mechanical complications, and degeneration of tissue valves.

Degradation of heart valve performance can be traced in part to deposits of plaque and calcified material on the valve. The leaflets of the valve are slightly thickened and coarse calcified particles and atheromatous deposits fill the belly of the valve cusps. For aortic stenosis, the buildup of calcified nodules occurs on the upper or superior surface of the aortic valve leaflets. These nodules decrease the flexibility of the leaflets, thereby limiting their mobility and capacity to fully open to permit adequate blood flow. Large calcifications in the sinus of the cusps also hinders the mobility of the valve. In addition, heavily calcified valve annulus presents a risk to the surgeon performing prosthetic aortic valve placement, as needles have difficulty in piercing calcified plaque and could fracture the plaque. Histological findings present fibrosis and calcification of the valvular annulus and the proximal parts of the cusps, with calcifications often extending to the commissures (the locations where the valve leaflets meet).

Unfortunately, current methods of repairing thickened and/or calcified valves through the removal of these deposits have significant disadvantages. Currently, high speed debriders, in combination with conventional mechanical instruments (e.g., forceps, rongeurs, scalpels), are used to removal calcified deposits. These mechanical methods are unsatisfactory as they produce tissue fragments which must be carefully and completely removed from the interior of the heart. Packs must be placed in the left ventricle to prevent the passage of calcified fragments into the heart. The area of treatment using conventional methods is also limited as general valve repair is usually not attempted if calcifications extends to the ventricular aspects of the cusps, if gross distortion of the normal architecture of the cusps is present, or if extensive commissural fusion is demonstrated.

Balloon-valvuloplasty, where a balloon catheter is inflated in the aortic valve to compress and fracture the calcified nodules in an attempt to increase leaflet mobility, has generally not been very effective in treating this type of stenosis. This is mainly because the calcified commissural parts of the cusps make it extremely difficult (if not impossible) to enlarge the valve area.

Lasers and ultrasound techniques for removing calcium deposits, though initially promising, cause deep tissue damage which permanently changes the characteristics of the valve leaflets. For example, when lasers are used for total leaflet debridement, they usually result in substantial tissue charring which causes thermal degradation of the connective tissue component of aortic valve leaflets. Damage to the connective tissue creates problems similar to those created by the calcium deposits (i.e. reduced mobility, flow regurgitation, etc.). Additionally, lasers are cumbersome to employ and have thus far been limited to in vitro debridement of aortic valves. Ultrasonic debridement of calcified deposits has similar drawbacks. Ultrasonic energy typically causes an intense healing response in the thin, flexible debrided leaflet that develops leaflet thickening and shrinkage. Such healing changes the flexural characteristics of the leaflet, creating high rates of post-procedure aortic insufficiency and regurgitation.

Accordingly, improved devices and methods are needed to decalcify heart valve leaflets while minimizing damage to the valves and substantially preserving the elastic fiber layer of the valve leaflets. The preservation of the elastic fiber layer of valve leaflets will play an important role in preventing later stenosis or regurgitation. Such an improved system would significantly enhance the options available to surgeons performing valve repair and replacement procedures.

SUMMARY OF THE INVENTION

The present invention provides systems, apparatus and methods for selectively applying electrical energy to structures in the heart such as the leaflets of the mitral and aortic valves. The systems and methods of the present invention are particularly useful for the volumetric removal or ablation of calcified deposits and fibroid material on valve leaflets to increase leaflet mobility, improving valve performance.

The method of the present invention comprises positioning an electrosurgical probe or catheter adjacent the target site so that one or more electrode terminal(s) are brought into at least partial contact or close proximity with calcified deposits or fibroid material on cardiac tissue. High frequency voltage is then applied between the electrode terminal(s) and one or more return electrode(s) to volumetrically remove or ablate at least a portion of the material while minimizing damage to the cardiac tissue. The present invention may be used for valve repair by debridement/ decalcification, performing a commissurotomy on valve leaflets that have been calcified shut, or to facilitate the removal of valves in replacement procedures by debriding/ decalcifying material along the annulus of the valve. In these procedures, the present invention removes calcified deposits from in and around the heart valves to improve mobility while minimizing damage to the valves and substantially preserving the elastic fiber layer of the valve leaflets.

In a specific aspect of the invention, a method is provided for repairing valves by removing calcified deposits from the cusps of valve leaflets. In this method, one or more electrode terminal(s) are delivered into the interior of the heart, either percutaneously (e.g., transluminally) or directly in a minimally invasive (e.g., Port Access™) or open procedure. In a preferred embodiment, an electrically conducting fluid is provided between the electrode terminal(s) and one or more return electrode(s) positioned proximal to the electrode terminal(s) to provide a current flow path from the electrode terminal(s) to the return electrode(s). The current flow path may be generated by directing an electrically conducting fluid along a fluid path past the return electrode and to the target site, or by locating a viscous electrically conducting fluid, such as a gel, at the target site, and submersing the electrode terminal(s) and the return electrode(s) within the conductive gel. In both embodiments, high frequency voltage is applied between the electrode terminal(s) and one or more return electrode(s) to volumetrically remove or ablate at least a portion of the calcified deposit. The high frequency voltage is preferably selected to effect controlled removal of calcified deposits without damaging the elastic fibers of the valve leaflet.

In preferred embodiments, the material is removed by molecular dissociation or disintegration processes. In these embodiments, the high frequency voltage applied to the electrode terminal(s) is sufficient to vaporize an electrically conductive fluid (e.g., gel or saline) between the electrode terminal(s) and the tissue. Within the vaporized fluid, an ionized plasma is formed and charged particles (e.g., electrons) are accelerated towards the tissue to cause the molecular breakdown or disintegration of several cell layers of the tissue. This molecular dissociation is accompanied by the volumetric removal of the tissue. The short range of the accelerated charged particles within the plasma layer confines the molecular dissociation process to the surface layer to minimize damage and necrosis to the underlying tissue. This process can be precisely controlled to effect the volumetric removal of tissue as thin as 10 to 150 microns with minimal heating of, or damage to, surrounding or underlying tissue structures. A more complete description of this phenomena is described in commonly assigned U.S. Pat. No. 5,683,366.

The present invention offers a number of advantages over current microdebrider, ultrasonic, and laser techniques for in vivo cardiac valve repair. The ability to precisely control the volumetric removal of material results in a field of tissue ablation or removal that is very defined, consistent and predictable. The shallow depth of tissue heating helps to minimize or completely eliminate damage to healthy valve structures adjacent to the target calcified deposits. In addition, the present invention completely removes or ablates the calcified deposits in situ without damaging or removing portions of the valve. Accordingly, the present invention generates little or no tissue fragments which must be removed from the interior of the heart. Moreover, since the present invention allows for the use of electrically conductive fluid (contrary to prior art electrosurgery techniques), isotonic saline may be used during the procedure. Saline is the preferred medium for irrigation because it has the same electrolyte concentration as the body's own cells and fluids and, therefore, is not absorbed into the body as much as other fluids.

Apparatus according to the present invention generally include an electrosurgical instrument having a shaft with proximal and distal ends, one or more electrode terminal(s) at the distal end and one or more connectors coupling the electrode terminal(s) to a source of high frequency electrical energy. In some embodiments, the instrument will comprise a catheter designed for percutaneous and/or transluminal delivery to the interior of the heart. In other embodiments, the instrument will comprise a more rigid probe designed for percutaneous (e.g., intercostal) or direct delivery to the heart in either open procedures or port access type procedures. In both embodiments, the apparatus will include a high frequency power supply for applying a high frequency voltage to the electrode terminal(s). The voltage is sufficient to volumetrically remove at least a portion of the calcified deposits from cardiac tissue in situ while minimizing damage to the healthy tissue.

The apparatus will preferably further include a fluid delivery element for delivering electrically conducting fluid to the electrode terminal(s) and the target site. The fluid delivery element may be located on the instrument, e.g., a fluid lumen or tube, or it may be part of a separate instrument. Alternatively, an electrically conducting gel or spray, such as a saline electrolyte or other conductive gel, may be applied to the target site (e.g., directly on the valve). In this embodiment, the apparatus may not have a fluid delivery element. In both embodiments, the electrically conducting fluid will preferably generate a current flow path between the electrode terminal(s) and one or more return electrode(s). In an exemplary embodiment, the return electrode is located on the instrument and spaced a sufficient distance from the electrode terminal(s) to substantially avoid or minimize current shorting therebetween and to shield the return electrode from tissue at the target site.

In a specific configuration, the electrosurgical instrument will include an electrically insulating electrode support member, preferably an inorganic support material (e.g., ceramic, glass, glass/ceramic, etc.) having a tissue treatment surface at the distal end of the instrument shaft. One or more electrode terminal(s) are coupled to, or integral with, the electrode support member such that the electrode terminal(s) are spaced from the return electrode. In one embodiment, the instrument includes an electrode array having a plurality of electrically isolated electrode terminals embedded into the electrode support member such that the electrode terminals extend about 0.0 mm to about 10 mm distally from the tissue treatment surface of the electrode support member. In this embodiment, the probe will further include one or more lumens for delivering electrically conductive fluid and/or aspirating the target site to one or more openings around the tissue treatment surface of the electrode support member. In an exemplary embodiment, the lumen will extend through a fluid tube exterior to the probe shaft that ends proximal to the return electrode.

BRIEF DESCRIPTION OF THE DRAWINGS

FIG. 6 is a perspective view of an alternative electrosurgical probe incorporating an inner fluid lumen.

DESCRIPTION OF SPECIFIC EMBODIMENTS

Figure 1:
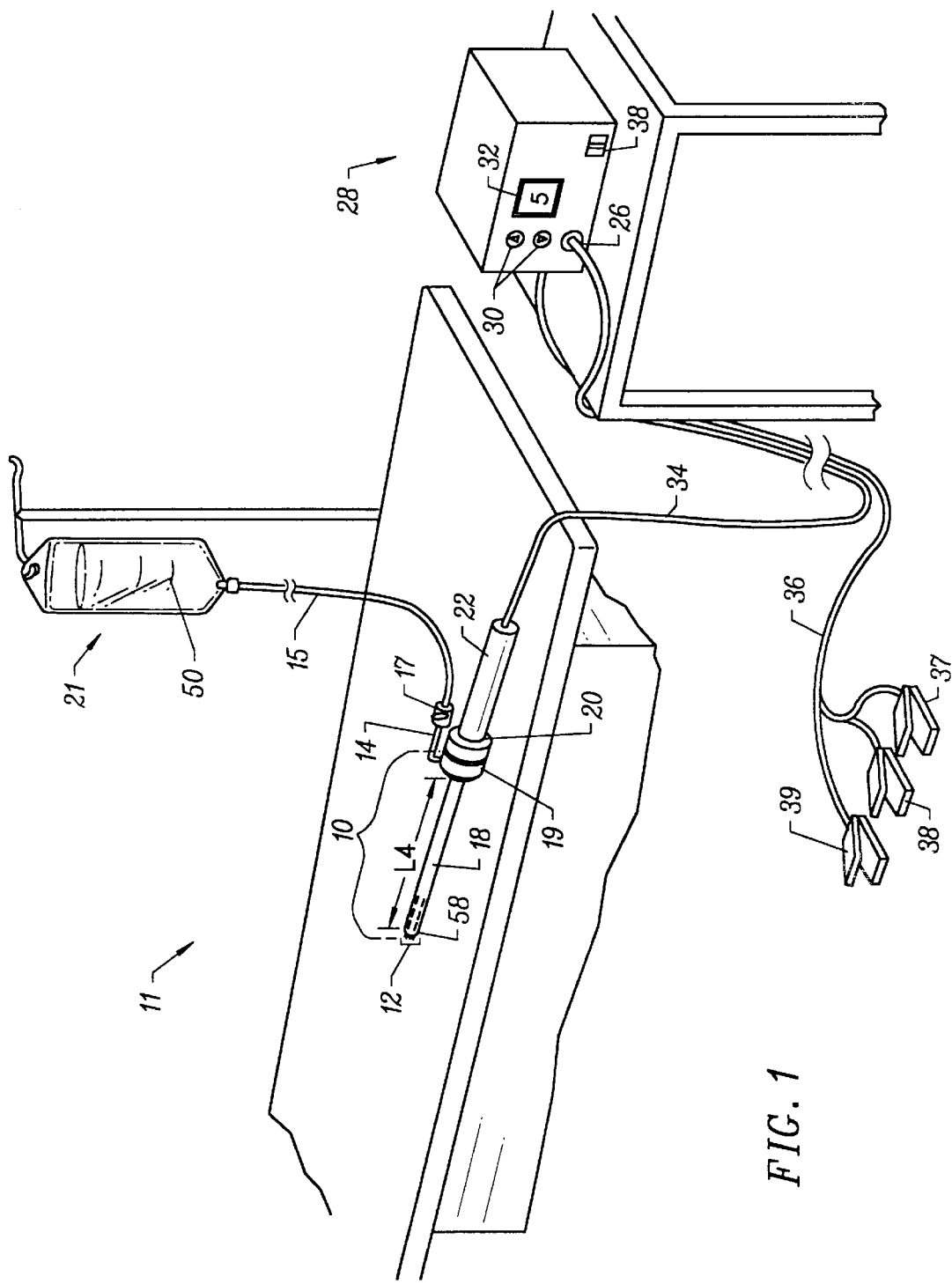
FIG. 1 is a perspective view of an electrosurgical system incorporating a power supply and an electrosurgical probe for tissue ablation, resection, incision, contraction and for vessel hemostasis according to the present invention.

The present invention provides systems and methods for selectively applying electrical energy to a target location within or on a patient's body, particularly including tissue in the heart such as the leaflets of the mitral and aortic valves. The methods and apparatus of the present invention are also useful for removing atheromatous material which partially or fully occludes a body lumen, such as a blood vessel. In fact, the methods and apparatus disclosed herein may be used in a wide variety of procedures, including open procedures, intravascular procedures, urology, laparascopy, arthroscopy, thoracoscopy or other cardiac procedures, dermatology, orthopedics, gynecology, otorhinolaryngology, spinal and neurologic procedures, oncology and the like. For convenience, the remaining disclosure will be directed specifically to the removal of undesirable material from cardiac tissue, such as calcified deposits or plaque.

In the present invention, high frequency (RF) electrical energy is applied to one or more electrode terminals in the presence of electrically conductive fluid to remove and/or modify the structure of tissue structures. Depending on the specific procedure, the present invention may be used to: (1) volumetrically remove tissue or cartilage (i.e., ablate or effect molecular dissociation of the tissue structure); (2) cut or resect tissue; (3) shrink or contract collagen connective tissue; and/or (4) coagulate severed blood vessels. During valve repair and/or replacement, the present invention is particularly useful for ablation and/or hemostasis. The calcified plaque deposits on the leaflets may be extremely hard and difficult to remove. The electrosurgical device of the present invention can cauterize and seal small blood vessels in tissue which may be exposed during valve leaflet removal. The present invention may be used to sculpt and remove calcified material surrounding valves to be repaired or replaced. This reduces the amount of obstructive material which may complicate placement of the prosthetic valve or facilitate a restenotic effect.

The techniques of the present invention may be performed percutaneously by introducing an electrosurgical instrument into the patient's vasculature and advancing the instrument transluminally to a target site. These procedures may also be performed through other minimally invasive methods such as port access or "key-hole" operations as under development by companies such as Heartport of Redwood City, Calif. and Cardiothoracic Systems of Portola Valley, Calif. These procedures may further be performed using traditional open surgery techniques. The present invention is particularly useful for removing small amounts of calcified tissue and other materials with minimal damage to the underlying valve leaflet and with minimal disruption of the elastic fiber layer in the valve leaflets. Maintaining the elasticity of the valves minimizes later stenosis or regurgitation of blood flow.

In the preferred method, calcified deposits and plaque on cardiac tissue are volumetrically removed or ablated. In this procedure, a high frequency voltage difference is applied between one or more electrode terminal(s) and one or more return electrode(s) to develop high electric field intensities in the vicinity of the target tissue. The high electric field intensities adjacent the electrode terminal(s) lead to electric field induced molecular breakdown of target tissue through molecular dissociation (rather than thermal evaporation or carbonization). Applicant believes that the tissue structure is volumetrically removed through molecular disintegration of larger organic molecules into smaller molecules and/or atoms, such as hydrogen, oxygen, oxides of carbon, hydrocarbons and nitrogen compounds. This molecular disintegration completely removes the tissue structure, as opposed to dehydrating the tissue material by the removal of liquid within the cells of the tissue, as is typically the case with electrosurgical desiccation and vaporization.

The high electric field intensities may be generated by applying a high frequency voltage that is sufficient to vaporize an electrically conducting fluid over at least a portion of the electrode terminal(s) in the region between the distal tip of the electrode terminal(s) and the target tissue. The electrically conductive fluid may be a liquid, such as isotonic saline or blood, delivered to the target site, or a viscous fluid, such as a gel, applied to the target site. Since the vapor layer or vaporized region has a relatively high electrical impedance, it increases the voltage differential between the electrode terminal tip and the tissue and causes ionization within the vapor layer due to the presence of an ionizable species (e.g., sodium when isotonic saline is the electrically conducting fluid). This ionization, under optimal conditions, induces the discharge of energetic electrons and photons from the vapor layer and to the surface of the target tissue. This energy may be in the form of energetic photons (e.g., ultraviolet radiation), energetic particles (e.g., electrons) or a combination thereof. A more detailed description of this phenomena, termed Coblation™ can be found in commonly assigned U.S. Pat. No. 5,683,366 the complete disclosure of which is incorporated herein by reference.

The present invention applies high frequency (RF) electrical energy in an electrically conducting fluid environment to remove (i.e., resect, cut or ablate) a tissue structure, and to seal transected vessels within the region of the target tissue. The present invention is particularly useful for sealing larger arterial vessels, e.g., on the order of 1 mm or greater. In some embodiments, a high frequency power supply is provided having an ablation mode, wherein a first voltage is applied to an electrode terminal sufficient to effect molecular dissociation or disintegration of the tissue, and a coagulation mode, wherein a second, lower voltage is applied to an electrode terminal (either the same or a different electrode) sufficient to achieve hemostasis of severed vessels within the tissue. In other embodiments, an electrosurgical instrument is provided having one or more coagulation electrode(s) configured for sealing a severed vessel, such as an arterial vessel, and one or more electrode terminals configured for either contracting the collagen fibers within the tissue or removing (ablating) the tissue, e.g., by applying sufficient energy to the tissue to effect molecular dissociation. In the latter embodiments, the coagulation electrode(s) may be configured such that a single voltage can be applied to coagulate with the coagulation electrode(s), and to ablate with the electrode terminal (s). In other embodiments, the power supply is combined with the coagulation instrument such that the coagulation electrode is used when the power supply is in the coagulation mode (low voltage), and the electrode terminal(s) are used when the power supply is in the ablation mode (higher voltage).

The present invention is also useful for removing or ablating tissue around nerves, such as spinal, visceral or cranial nerves, e.g., the olfactory nerve on either side of the nasal cavity, the optic nerve within the optic and cranial canals, the palatine nerve within the nasal cavity, soft palate, uvula and tonsil, etc. One of the significant drawbacks with prior art mechanical cutters and lasers is that these devices do not differentiate between the target tissue and the surrounding nerves or bone. Therefore, the surgeon must be extremely careful during these procedures to avoid damage to the bone or nerves within and around the nasal cavity. In the present invention, the Coblation process for removing tissue results in extremely small depths of collateral tissue damage as discussed above. This allows the surgeon to remove tissue close to a nerve without causing collateral damage to the nerve fibers. A more complete description of this phenomena can be found in co-pending U.S. patent application. No. 09/032,375, filed Feb. 27, 1998 (Attorney Docket No. CB-3), the complete disclosure of which is incorporated herein by reference.

In the method of the present invention, one or more electrode terminals are brought into close proximity to tissue at a target site, and the power supply is activated in the ablation mode such that sufficient voltage is applied between the electrode terminals and the return electrode to volumetrically remove the tissue through molecular dissociation, as described below. During this process, vessels within the tissue will be severed. Smaller vessels will be automatically sealed with the system and method of the present invention. Larger vessels, and those with a higher flow rate, such as arterial vessels, may not be automatically sealed in the ablation mode. In these cases, the severed vessels may be sealed by activating a control (e.g., a foot pedal) to reduce the voltage of the power supply into the coagulation mode. In this mode, the electrode terminals may be pressed against the severed vessel to provide sealing and/or coagulation of the vessel. Alternatively, a coagulation electrode located on the same or a different instrument may be pressed against the severed vessel. Once the vessel is adequately sealed, the surgeon activates a control (e.g., another foot pedal) to increase the voltage of the power supply back into the ablation mode.

The electrosurgical instrument will comprise a shaft having a proximal end and a distal end which supports one or more electrode terminal(s). The shaft may assume a wide variety of configurations, with the primary purpose being to mechanically support one or more electrode terminal(s) and permit the treating physician to manipulate the electrode(s) from a proximal end of the shaft. Usually, an electrosurgical probe shaft will be a narrow-diameter rod or tube, more usually having dimensions which permit it to be introduced into a body cavity, such as the thoracic cavity, through an associated trocar or cannula in a minimally invasive procedure, such as arthroscopic, laparoscopic, thoracoscopic (e.g., Port Access™) and other endoscopic procedures. Thus, the probe shaft will typically have a length of at least 5 cm for open procedures and at least 10 cm, more typically being 20 cm, or longer for endoscopic procedures. The probe shaft will typically have a diameter of at least 1 mm and frequently in the range from 1 to 10 mm.

The electrosurgical instrument may be delivered percutaneously and/or endoluminally to the ventricular cavity of the heart by insertion through a conventional or specialized guide catheter, or the invention may include a catheter having an active electrode or electrode array integral with its distal end. The catheter shaft may be rigid or flexible, with flexible shafts optionally being combined with a generally rigid external tube for mechanical support. Flexible shafts may be combined with pull wires, shape memory actuators, and other known mechanisms for effecting selective deflection of the distal end of the shaft to facilitate positioning of the electrode or electrode array. The catheter haft will usually include a plurality of wires or other conductive elements running axially therethrough to permit connection of the electrode or electrode array and the return electrode to a connector at the proximal end of the catheter shaft. The catheter shaft may include a guide wire for guiding the catheter to the target site, or the catheter may comprise a steerable guide catheter. The catheter may also include a substantially rigid distal end portion to increase the torque control of the distal end portion as the catheter is advanced further into the patient's body. Specific shaft designs will be described in detail in connection with the figures hereinafter.

The electrode terminal(s) are preferably supported within or by an inorganic insulating support positioned near the distal end of the instrument shaft, e.g., a catheter body. The return electrode may be located on the instrument shaft, on another instrument or on the external surface of the patient (i.e., a dispersive pad). The close proximity of the heart, however, makes a bipolar design more preferable because this minimizes the current low through heart tissue. Accordingly, the return electrode is preferably either integrated with the catheter body, or another instrument located in close proximity to the distal end of he catheter body. The proximal end of the catheter will include the appropriate electrical connections for coupling the return electrode(s) and the electrode terminal(s) to a high frequency power supply, such as an electrosurgical generator.

The current flow path between the electrode terminals and the return electrode(s) may be generated by submerging the tissue site in an electrical conducting fluid (e.g., within a viscous fluid, such as an electrically conductive gel) or by directing an electrically conducting fluid along a fluid path to the target site (i.e., a liquid, such as isotonic saline, or a gas, such as argon). The conductive gel may also be delivered to the target site to achieve a slower more controlled delivery rate of conductive fluid. In addition, the viscous nature of the gel may allow the surgeon to more easily contain the gel around the target site (e.g., rather than attempting to contain isotonic saline). A more complete description of an exemplary method of directing electrically conducting fluid between the active and return electrodes is described in U.S. Pat. No. 5,697,281, previously incorporated herein by reference. Alternatively, the body's natural conductive fluids, such as blood, may be sufficient to establish a conductive path between the return electrode(s) and the electrode terminal(s), and to provide the conditions for establishing a vapor layer, as described above. Advantageously, a liquid electrically conductive fluid (e.g., isotonic saline) may be used to concurrently "bathe" the target tissue surface to provide an additional means for removing any tissue, and to cool the region of the target tissue ablated in the previous moment.

The power supply may include a fluid interlock for interrupting power to the electrode terminal(s) when there is insufficient conductive fluid around the electrode terminal (s). This ensures that the instrument will not be activated when conductive fluid is not present, minimizing the tissue damage that may otherwise occur. A more complete description of such a fluid interlock can be found in commonly assigned, co-pending U.S. application. Ser. No. 09/058,336, filed Apr. 10, 1998 (attorney Docket No. CB-4), the complete disclosure of which is incorporated herein by reference.

In some procedures, it may also be necessary to retrieve or aspirate the electrically conductive fluid and/or the non-condensible gaseous products of ablation. For example, in procedures in and around the heart, or within blood vessels, it may be desirable to aspirate the fluid so that it does not flow downstream. In addition, it may be desirable to aspirate small pieces of tissue or calcium fragments that are not completely disintegrated by the high frequency energy, or other fluids at the target site, such as blood, mucus, the gaseous products of ablation, etc. Accordingly, the system of the present invention may include one or more suction lumen(s) in the instrument, or on another instrument, coupled to a suitable vacuum source for aspirating fluids from the target site.

As an alternative or in addition to suction, it may be desirable to contain the excess electrically conductive fluid, tissue fragments and/or gaseous products of ablation at or near the target site with a containment apparatus, such as a basket, retractable sheath or the like. This embodiment has the advantage of ensuring that the conductive fluid, tissue fragments or ablation products do not flow into the heart or lungs. In addition, it may be desirable to limit the amount of suction to limit the undesirable effect suction may have on hemostasis of severed blood vessels within heart tissue.

The present invention may use a single active electrode terminal or an array of electrode terminals spaced around the distal surface of a catheter or probe. In the latter embodiment, the electrode array usually includes a plurality of independently current-limited and/or power-controlled electrode terminals to apply electrical energy selectively to the target tissue while limiting the unwanted application of electrical energy to the surrounding tissue and environment resulting from power dissipation into surrounding electrically conductive fluids, such as blood, normal saline, and the like. The electrode terminals may be independently current-limited by isolating the terminals from each other and connecting each terminal to a separate power source that is isolated from the other electrode terminals. Alternatively, the electrode terminals may be connected to each other at either the proximal or distal ends of the catheter to form a single wire that couples to a power source.

In one configuration, each individual electrode terminal in the electrode array is electrically insulated from all other electrode terminals in the array within said instrument and is connected to a power source which is isolated from each of the other electrode terminals in the array or to circuitry which limits or interrupts current flow to the electrode terminal when low resistivity material (e.g., blood, electrically conductive saline irrigant or electrically conductive gel) causes a lower impedance path between the return electrode and the individual electrode terminal. The isolated power sources for each individual electrode terminal may be separate power supply circuits having internal impedance characteristics which limit power to the associated electrode terminal when a low impedance return path is encountered. By way of example, the isolated power source may be a user selectable constant current source. In this embodiment, lower impedance paths will automatically result in lower resistive heating levels since the heating is proportional to the square of the operating current times the impedance. Alternatively, a single power source may be connected to each of the electrode terminals through independently actuatable switches, or by independent current limiting elements, such as inductors, capacitors, resistors and/or combinations thereof. The current limiting elements may be provided in the instrument, connectors, cable, controller or along the conductive path from the controller to the distal tip of the instrument. Alternatively, the resistance and/or capacitance may occur on the surface of the active electrode terminal(s) due to oxide layers which form selected electrode terminals (e.g., titanium or a resistive coating on the surface of metal, such as platinum).

The tip region of the instrument may comprise many independent electrode terminals designed to deliver electrical energy in the vicinity of the tip. The selective application of electrical energy to the conductive fluid is achieved by connecting each individual electrode terminal and the return electrode to a power source having independently controlled or current limited channels. The return electrode(s) may comprise a single tubular member of conductive material proximal to the electrode array at the tip which also serves as a conduit for the supply of the electrically conducting fluid between the active and return electrodes. Alternatively, the instrument may comprise an array of return electrodes at the distal tip of the instrument (together with the active electrodes) to maintain the electric current at the tip. The application of high frequency voltage between the return electrode(s) and the electrode array results in the generation of high electric field intensities at the distal tips of the electrode terminals with conduction of high frequency current from each individual electrode terminal to the return electrode. The current flow from each individual electrode terminal to the return electrode(s) is controlled by either active or passive means, or a combination thereof, to deliver electrical energy to the surrounding conductive fluid while minimizing energy delivery to surrounding (non-target) tissue.

The application of a high frequency voltage between the return electrode(s) and the electrode terminal(s) for appropriate time intervals effects cutting, removing, ablating, shaping, contracting or otherwise modifying the target tissue. The tissue volume over which energy is dissipated (i.e., a high current density exists) may be precisely controlled, for example, by the use of a multiplicity of small electrode terminals whose effective diameters or principal dimensions range from about 5 mm to 0.01 mm, preferably from about 2 mm to 0.05 mm, and more preferably from about 1 mm to 0.1 mm. Electrode areas for both circular and non-circular terminals will have a contact area (per electrode terminal) below 25 $mm^2$ for electrode arrays and as large as 75 $mm^2$ for single electrode embodiments, preferably being in the range from 0.0001 $mm^2$ to 1 $mm^2$, and more preferably from 0.005 $mm^2$ to 0.5 $mm^2$. The circumscribed area of the electrode array is in the range from 0.25 $mm^2$ to 75 $mm^2$, preferably from 0.5 $mm^2$ to 40 $mm^2$, and will usually include at least one includes, often at least two isolated electrode terminals, often at least five electrode terminals, often greater than 10 electrode terminals and even 50 or more electrode terminals, disposed over the distal contact surfaces on the shaft. The use of small diameter electrode terminals increases the electric field intensity and reduces the extent or depth of tissue heating as a consequence of the divergence of current flux lines which emanate from the exposed surface of each electrode terminal.

The area of the tissue treatment surface can vary widely, and the tissue treatment surface can assume a variety of geometries, with particular areas and geometries being selected for specific applications. The active electrode surface(s) can have area(s) in the range from 0.25 $mm^2$ to 75 $mm^2$, usually being from about 0.5 $mm^2$ to 40 $mm^2$. The geometries can be planar, concave, convex, hemispherical, conical, linear "in-line" array or virtually any other regular or irregular shape. Most commonly, the active electrode(s) or electrode terminal(s) will be formed at the distal tip of the electrosurgical instrument shaft, frequently being planar, disk-shaped, or hemispherical surfaces for use in reshaping procedures or being linear arrays for use in cutting. Alternatively or additionally, the active electrode(s) may be formed on lateral surfaces of the electrosurgical instrument shaft (e.g., in the manner of a spatula), facilitating access to certain body structures in endoscopic procedures.

In some embodiments, the electrode support and the fluid outlet may be recessed from an outer surface of the instrument or handpiece to confine the electrically conductive fluid to the region immediately surrounding the electrode support. In addition, the shaft may be shaped so as to form a cavity around the electrode support and the fluid outlet. This helps to assure that the electrically conductive fluid will remain in contact with the electrode terminal(s) and the return electrode(s) to maintain the conductive path therebetween. In addition, this will help to maintain a vapor layer and subsequent plasma layer between the electrode terminal (s) and the tissue at the treatment site throughout the procedure, which reduces the thermal damage that might otherwise occur if the vapor layer were extinguished due to a lack of conductive fluid. Provision of the electrically conductive fluid around the target site also helps to maintain the tissue temperature at desired levels.

The electrically conducting fluid should have a threshold conductivity to provide a suitable conductive path between the return electrode and the electrode terminal(s). The electrical conductivity of the fluid (in units of milliSiemans per centimeter or mS/cm) will usually be greater than 0.2 mS/cm, preferably will be greater than 2 mS/cm and more preferably greater than 10 mS/cm. In an exemplary embodiment, the electrically conductive fluid is isotonic saline, which has a conductivity of about 17 mS/cm.

The voltage difference applied between the return electrode(s) and the electrode terminal(s) will be at high or radio frequency, typically between about 5 kHz and 20 MHz, usually being between about 30 kHz and 2.5 MHz, preferably being between about 50 kHz and 500 kHz, more preferably less than 350 kHz, and most preferably between about 100 kHz and 200 kHz. The RMS (root mean square) voltage applied will usually be in the range from about 5 volts to 1000 volts, preferably being in the range from about 10 volts to 500 volts depending on the electrode terminal size, the operating frequency and the operation mode of the particular procedure or desired effect on the tissue (i.e., contraction, coagulation, cutting or ablation). Typically, the peak-to-peak voltage for ablation or cutting will be in the range of 10 to 2000 volts and preferably in the range of 200 to 1800 volts and more preferably in the range of about 300 to 1500 volts, often in the range of about 500 to 900 volts peak to peak (again, depending on the electrode size, the operating frequency and the operation mode). Lower peak-to-peak voltages will be used for tissue coagulation or collagen contraction and will typically be in the range from 50 to 1500, preferably 100 to 1000 and more preferably 120 to 600 volts peak-to-peak.

As discussed above, the voltage is usually delivered in a series of voltage pulses or alternating current of time varying voltage amplitude with a sufficiently high frequency (e.g., on the order of 5 kHz to 20 MHz) such that the voltage is effectively applied continuously (as compared with e.g., lasers claiming small depths of necrosis, which are generally pulsed about 10 to 20 Hz). In addition, the duty cycle (i.e., cumulative time in any one-second interval that energy is applied) is on the order of about 50% for the present invention, as compared with pulsed lasers which typically have a duty cycle of about 0.0001%.

The preferred power source of the present invention delivers a high frequency current selectable to generate average power levels ranging from several milliwatts to tens of watts per electrode, depending on the volume of target tissue being heated, and/or the maximum allowed temperature selected for the instrument tip. The power source allows the user to select the voltage level according to the specific requirements of a particular cardiac surgery, arthroscopic surgery, dermatological procedure, ophthalmic procedures, open surgery or other endoscopic surgery procedure. For cardiac procedures, the power source may have an additional filter, for filtering leakage voltages at frequencies below 100 kHz, particularly voltages around 60 kHz. A description of a suitable power source can be found in co-pending patent applications Ser. Nos. 09/058,571 and 09/058,336, filed Apr. 10, 1998 (Attorney Docket Nos. CB-2 and CB-4), the complete disclosure of both applications are incorporated herein by reference for all purposes.

The power source may be current limited or otherwise controlled so that undesired heating of the target tissue or surrounding (non-target) tissue does not occur. In a presently preferred embodiment of the present invention, current limiting inductors are placed in series with each independent electrode terminal, where the inductance of the inductor is in the range of 10 uH to 50,000 uH, depending on the electrical properties of the target tissue, the desired tissue heating rate and the operating frequency. Alternatively, capacitor-inductor (LC) circuit structures may be employed, as described previously in U.S. Pat. No. 5,697,909, the complete disclosure of which is incorporated herein by reference. Additionally, current limiting resistors may be selected. Preferably, these resistors will have a large positive temperature coefficient of resistance so that, as the current level begins to rise for any individual electrode terminal in contact with a low resistance medium (e.g., saline irrigant or blood), the resistance of the current limiting resistor increases significantly, thereby minimizing the power delivery from said electrode terminal into the low resistance medium (e.g., saline irrigant or blood).

In yet another aspect of the invention, the control system is "tuned" so that it will not apply excessive power to the blood (e.g., in the ventricle), once it crosses the wall of the heart and enters the chamber of the left ventricle. This minimizes the formation of a thrombus in the heart (i.e., will not induce thermal coagulation of the blood). The control system may include an active or passive architecture, and will typically include a mechanism for sensing resistance between a pair(s) of active electrodes at the distal tip, or between one or more active electrodes and a return electrode, to sense when the electrode array has entered into the blood-filled chamber of the left ventricle. Alternatively, current limiting means may be provided to prevent sufficient joulean heating in the lower resistivity blood to cause thermal coagulation of the blood. In another alternative embodiment, an ultrasound transducer at the tip of the instrument can be used to detect the boundary between the abnormal tissue layer (e.g., calcified deposits) and healthy underlying tissue.

It should be clearly understood that the invention is not limited to electrically isolated electrode terminals, or even to a plurality of electrode terminals. For example, the array of active electrode terminals may be connected to a single lead that extends through the catheter shaft to a power source of high frequency current. Alternatively, the catheter may incorporate a single electrode that extends directly through the catheter shaft or is connected to a single lead that extends to the power source. The active electrode(s) may have ball shapes (e.g., for tissue vaporization and desiccation), twizzle shapes (for vaporization and needle-like cutting), spring shapes (for rapid tissue debulking and desiccation), twisted metal shapes, annular or solid tube shapes or the like. Alternatively, the electrode(s) may comprise a plurality of filaments, rigid or flexible brush electrode(s) (for debulking a tumor, such as a fibroid, bladder tumor or a prostate adenoma), side-effect brush electrode(s) on a lateral surface of the shaft, coiled electrode(s) or the like.

In one embodiment, an electrosurgical catheter or probe comprises a single active electrode terminal that extends from an insulating member, e.g., ceramic, at the distal end of the shaft. The insulating member is preferably a tubular structure that separates the active electrode terminal from a tubular or annular return electrode positioned proximal to the insulating member and the active electrode. In another embodiment, the catheter or probe includes a single active electrode that can be rotated relative to the rest of the catheter body, or the entire catheter may be rotated related to the lead. The single active electrode can be positioned adjacent the abnormal tissue (e.g., calcified deposits) and energized and rotated as appropriate to remove this tissue.

The current flow path between the electrode terminal(s) and the return electrode(s) may be generated by submerging the tissue site in an electrical conducting fluid (e.g., within a viscous fluid, such as an electrically conductive gel) or by directing an electrically conducting fluid along a fluid path to the target site (i.e., a liquid, such as isotonic saline, or a gas, such as argon). This latter method is particularly effective in a dry environment (i.e., the tissue is not submerged in fluid) because the electrically conducting fluid provides a suitable current flow path from the electrode terminal to the return electrode.

Referring to FIG. 1, an exemplary electrosurgical system 11 for treatment of tissue in the cardiothoracic region will now be described in detail. Electrosurgical system 11 generally comprises an electrosurgical handpiece or probe 10 connected to a power supply 28 for providing high frequency voltage to a target site and a fluid source 21 for supplying electrically conducting fluid 50 to probe 10. In addition, electrosurgical system 11 may include an endoscope (not shown) with a fiber optic head light for viewing the surgical site, if desired. The endoscope may be integral with probe 10, or it may be part of a separate instrument. The system 11 may also include a vacuum source (not shown) for coupling to a suction lumen or tube 220 (see FIG. 2) in the probe 10 for aspirating the target site.

As shown, probe 10 generally includes a proximal handle 19 and an elongate shaft 18 having an array 12 of electrode terminals 58 at its distal end. A connecting cable 34 has a connector 26 for electrically coupling the electrode terminals 58 to power supply 28. The electrode terminals 58 are electrically isolated from each other and each of the terminals 58 is connected to an active or passive control network within power supply 28 by means of a plurality of individually insulated conductors (not shown). A fluid supply tube 15 is connected to a fluid tube 14 of probe 10 for supplying electrically conductive fluid 50 to the target site. Conductive fluid 50 may be driven by gravity or with a suitable pump.

Power supply 28 has an operator controllable voltage level adjustment 30 to change the applied voltage level, which is observable at a voltage level display 32. Power supply 28 also includes first, second and third foot pedals 37, 38, 39 and a cable 36 which is removably coupled to power supply 28. The foot pedals 37, 38, 39 allow the surgeon to remotely adjust the energy level applied to electrode terminals 58. In an exemplary embodiment, first foot pedal 37 is used to place the power supply into the "ablation" mode and second foot pedal 38 places power supply 28 into the "subablation" mode (e.g., coagulation, tissue contraction or the like). The third foot pedal 39 allows the user to adjust the voltage level within the "ablation" mode. In the ablation mode, a sufficient voltage is applied to the electrode terminals to establish the requisite conditions for molecular dissociation of the tissue (i.e., vaporizing a portion of the electrically conductive fluid, ionizing charged particles within the vapor layer and accelerating these charged particles against the tissue). As discussed above, the requisite voltage level for ablation will vary depending on the number, size, shape and spacing of the electrodes, the distance in which the electrodes extend from the support member, etc. Once the surgeon places the power supply in the "ablation" mode, voltage level adjustment 30 or third foot pedal 39 may be used to adjust the voltage level to adjust the degree or aggressiveness of the ablation.

Of course, it will be recognized that the voltage and modality of the power supply may be controlled by other input devices. However, applicant has found that foot pedals are convenient methods of controlling the power supply while manipulating the probe during a surgical procedure.

In the subablation mode, the power supply 28 applies a low enough voltage to the electrode terminals to avoid vaporization of the electrically conductive fluid and subsequent molecular dissociation of the tissue. The surgeon may automatically toggle the power supply between the ablation and subablation modes by alternatively stepping on foot pedals 37, 38, respectively. This allows, for example, the surgeon to quickly move between coagulation and ablation in situ, without having to remove his/her concentration from the surgical field or without having to request an assistant to switch the power supply. By way of example, as the surgeon is sculpting soft tissue in the ablation mode, the probe typically will simultaneously seal and/or coagulation small severed vessels within the tissue. However, larger vessels, or vessels with high fluid pressures (e.g., arterial vessels) may not be sealed in the ablation mode. Accordingly, the surgeon can simply step on foot pedal 38, automatically lowering the voltage level below the threshold level for ablation, and apply sufficient pressure onto the severed vessel for a sufficient period of time to seal and/or coagulate the vessel. After this is completed, the surgeon may quickly move back into the ablation mode by stepping on foot pedal 37. A specific design of a suitable power supply for use with the present invention can be found in co-pending patent applications Ser. Nos. 09/058,571 and 09/058,336, filed Apr. 10, 1998 (Attorney Docket Nos. CB-2 and CB-4), previously incorporated herein by reference.

Figure 2:
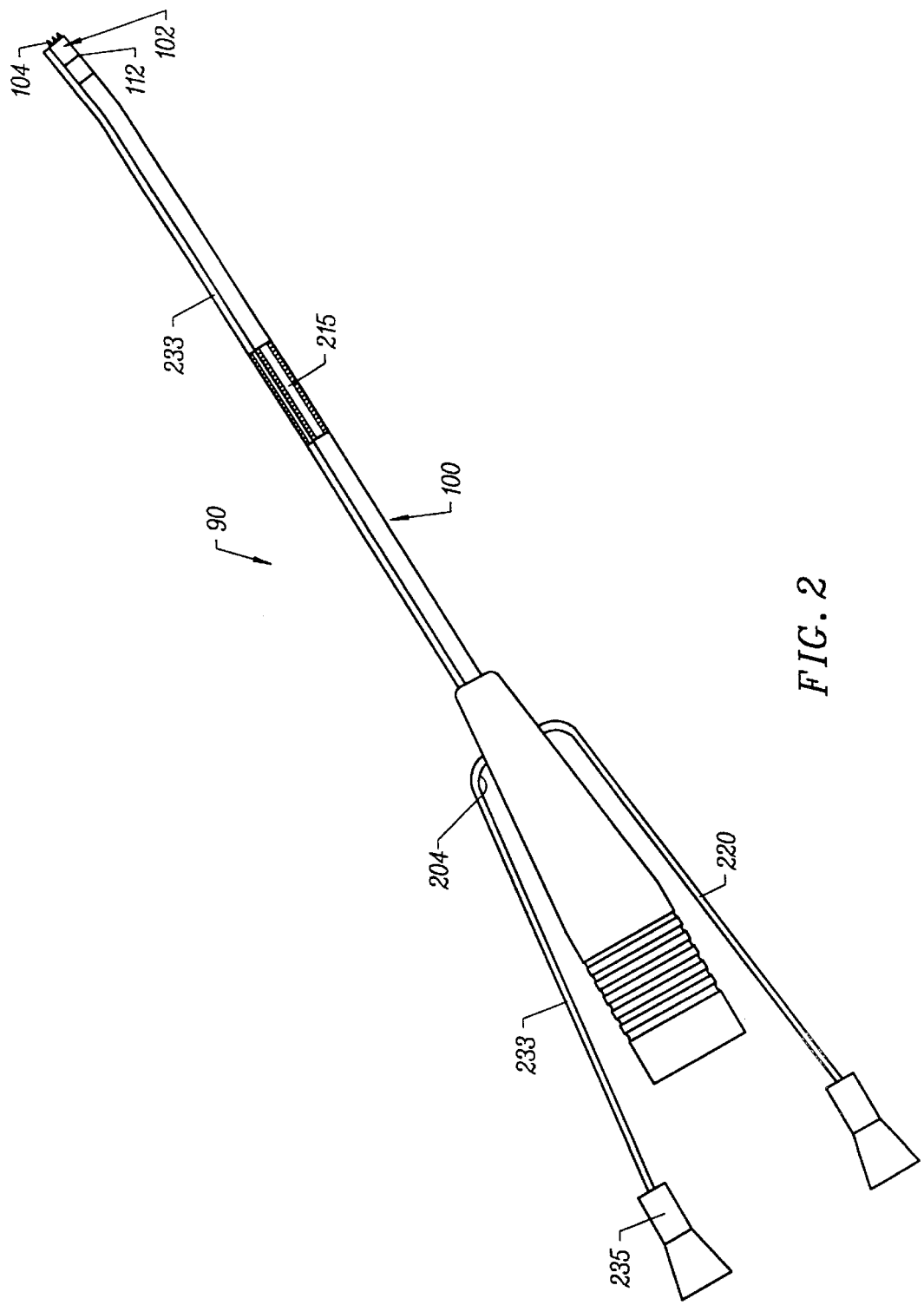
FIG. 2 is a side view of an electrosurgical probe according to the present invention.

FIGS. 2–5 illustrate an exemplary electrosurgical probe 90 constructed according to the principles of the present invention. As shown in FIG. 2, probe 90 generally includes an elongated shaft 100 which may be flexible or rigid, a handle 204 coupled to the proximal end of shaft 100 and an electrode support member 102 coupled to the distal end of shaft 100. Shaft 100 preferably comprises a plastic material that is easily molded into the shape shown in FIG. 1. Alternatively, shaft 100 may comprise an electrically conducting material, usually metal, which is selected from the group comprising tungsten, stainless steel alloys, platinum or its alloys, titanium or its alloys, molybdenum or its alloys, and nickel or its alloys. In this embodiment, shaft 100 includes an electrically insulating jacket, which is typically formed as one or more electrically insulating sheaths or coatings, such as polytetrafluoroethylene, polyimide, and the like. The provision of the electrically insulating jacket over the shaft prevents direct electrical contact between these metal elements and any adjacent body structure or the surgeon. Such direct electrical contact between a body structure (e.g., tendon) and an exposed electrode could result in unwanted heating and necrosis of the structure at the point of contact causing necrosis.

Handle 204 typically comprises a plastic material that is easily molded into a suitable shape for handling by the surgeon. Handle 204 defines an inner cavity (not shown) that houses the electrical connections 250 (FIG. 5), and provides a suitable interface for connection to an electrical connecting cable 22 (see FIG. 1). Electrode support member 102 extends from the distal end of shaft 100 (usually about 1 to 20 mm), and provides support for a plurality of electrically isolated electrode terminals 104 (see FIGS. 3 and 4). As shown in FIG. 2, a fluid tube 233 extends through an opening in handle 204, and includes a connector 235 for connection to a fluid supply source, for supplying electrically conductive fluid to the target site. Depending on the configuration of the distal surface of shaft 100, fluid tube 233 may extend through a single lumen (not shown) in shaft 100, or it may be coupled to a plurality of lumens (also not shown) that extend through shaft 100 to a plurality of openings at its distal end. In the representative embodiment, fluid tube 233 extends along the exterior of shaft 100 to a point just proximal of return electrode 112 (see FIG. 4). In this embodiment, the fluid is directed through an opening 237 past return electrode 112 to the electrode terminals 104. Probe 90 may also include a valve 17 (FIG. 1) or equivalent structure for controlling the flow rate of the electrically conducting fluid to the target site.

As shown in FIG. 2, the distal portion of shaft 100 is preferably bent to improve access to the operative site of the tissue being treated. Electrode support member 102 has a substantially planar tissue treatment surface 212 (FIG. 3) that is usually at an angle of about 10 to 90 degrees relative to the longitudinal axis of shaft 100, although the shaft may have no angle at all. In alternative embodiments, the distal portion of shaft 100 comprises a flexible material which can be deflected relative to the longitudinal axis of the shaft. Such deflection may be selectively induced by mechanical tension of a pull wire, for example, or by a shape memory wire that expands or contracts by externally applied temperature changes.

In the embodiment shown in FIGS. 2–5, probe 90 includes a return electrode 112 for completing the current path between electrode terminals 104 and a high frequency power supply 28 (see FIG. 1). As shown, return electrode 112 preferably comprises an annular conductive band coupled to the distal end of shaft 100 slightly proximal to tissue treatment surface 212 of electrode support member 102, typically about 0.5 to 10 mm and more preferably about 1 to 10 mm. In embodiments where the shaft comprises a conductive material, the shaft will have an exposed portion that functions as the return electrode. Return electrode 112 is coupled to a connector (not shown) that extends to the proximal end of probe 10, where it is suitably connected to power supply 10 (FIG. 1).

As shown in FIG. 2, return electrode 112 is not directly connected to electrode terminals 104. To complete this current path so that electrode terminals 104 are electrically connected to return electrode 112, electrically conducting fluid (e.g., isotonic saline) is caused to flow therebetween. In the representative embodiment, the electrically conducting fluid is delivered through fluid tube 233 to opening 237, as described above. Alternatively, the fluid may be delivered by a fluid delivery element (not shown) that is separate from probe 90. In arthroscopic surgery, for example, the body cavity will be flooded with isotonic saline and the probe 90 will be introduced into this flooded cavity. Electrically conducting fluid will be continually resupplied to maintain the conduction path between return electrode 112 and electrode terminals 104.

In alternative embodiments, the fluid path may be formed in probe 90 by, for example, an inner lumen or an annular gap between the return electrode and a tubular support member within shaft 100 (see FIG. 6). This annular gap may be formed near the perimeter of the shaft 100 such that the electrically conducting fluid tends to flow radially inward towards the target site, or it may be formed towards the center of shaft 100 so that the fluid flows radially outward.

In both of these embodiments, a fluid source (e.g., a bag of fluid elevated above the surgical site or suitable pumping device), is coupled to probe 90 via a fluid supply tube (not shown) that may or may not have a controllable valve.

Figure 3:
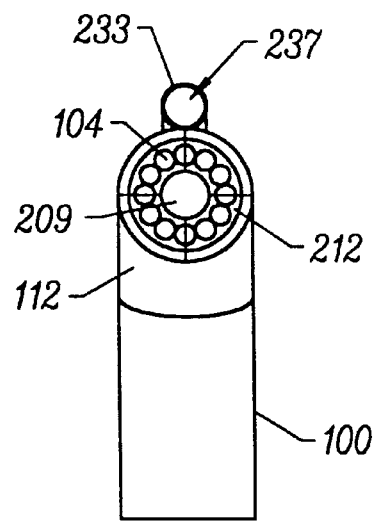
FIG. 3 is an end view of the probe of FIG. 2.

Referring to FIG. 3, the electrically isolated electrode terminals 104 are spaced apart over tissue treatment surface 212 of electrode support member 102. The tissue treatment surface and individual electrode terminals 104 will usually have dimensions within the ranges set forth above. In the representative embodiment, the tissue treatment surface 212 has a circular cross-sectional shape with a diameter in the range of about 1 to 20 mm. The individual electrode terminals 104 preferably extend outward from tissue treatment surface 212 by a distance of about 0.0 to 4 mm, usually about 0.2 to 2 mm. Applicant has found that this configuration increases the high electric field intensities and associated current densities around electrode terminals 104 to facilitate the ablation of tissue as described in detail above.

In the embodiment of FIGS. 2–5, the probe includes a single, larger opening 209 in the center of tissue treatment surface 212, and a plurality of electrode terminals (e.g., about 3 to 15 electrode terminals) around the perimeter of surface 212 (see FIG. 3). Alternatively, the probe may include a single, annular, or partially annular, electrode terminal at the perimeter of the tissue treatment surface. The central opening 209 is coupled to a suction lumen 215 within shaft 100 and a suction tube 211 (FIG. 2) for aspirating tissue, fluids, calcified fragments and/or gases from the target site. In this embodiment, the electrically conductive fluid generally flows radially inward past electrode terminals 104 and then back through the opening 209. Aspirating the electrically conductive fluid during surgery allows the surgeon to see the target site, and it prevents the dispersal of gases, tissue fragments and/or calcified deposits into the patient's body.

In some embodiments, the probe 90 will also include one or more aspiration electrode(s) (not shown) coupled to the aspiration lumen 215 for inhibiting clogging during aspiration of tissue fragments from the surgical site. A more complete description of these embodiments can be found in commonly assigned co-pending application Ser. No. 09/010,382, filed Jan. 21, 1998 (Attorney Docket No. A-6), the complete disclosure of which is incorporated herein by reference for all purposes.

Figure 5:
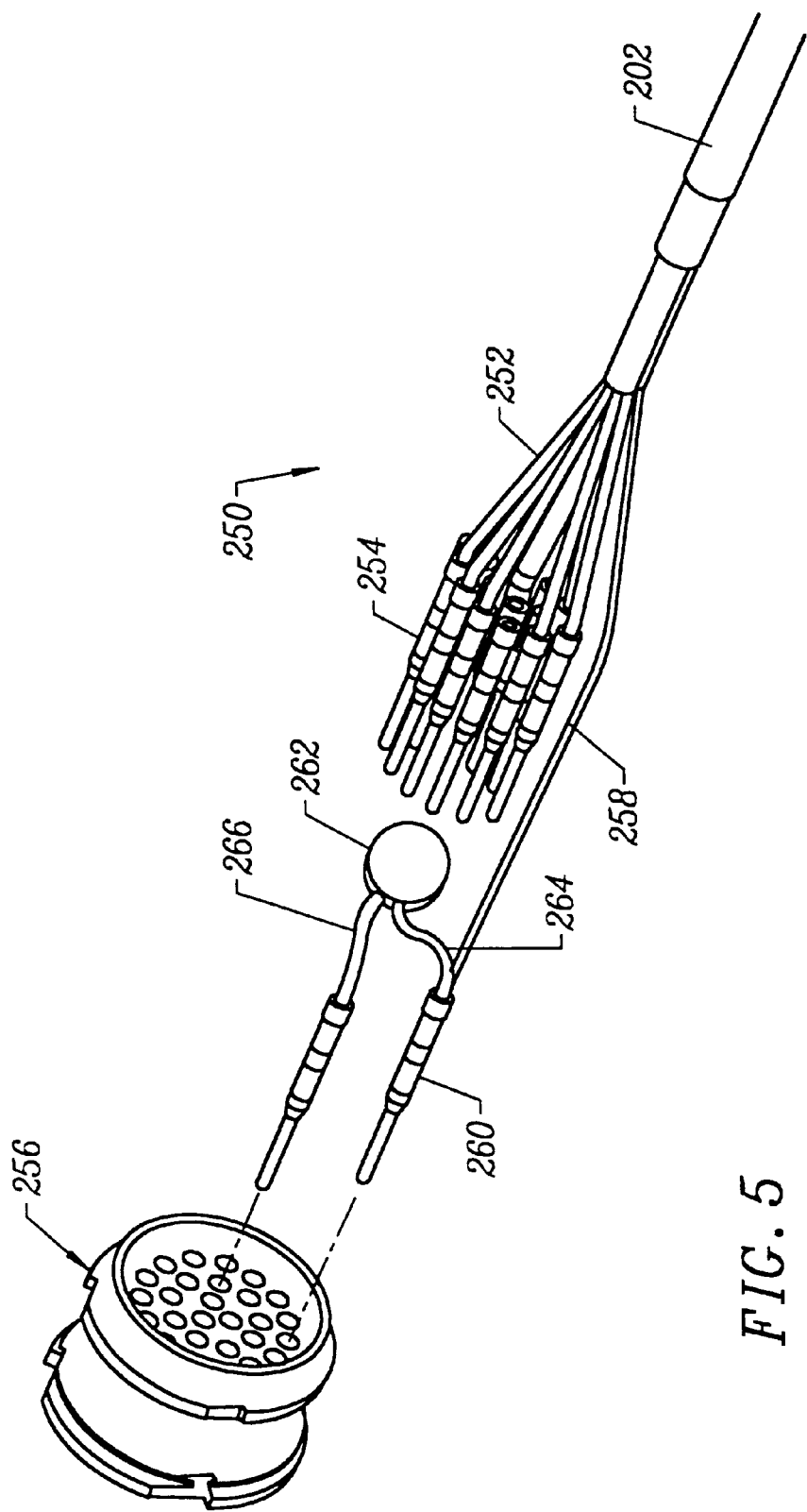
FIG. 5 is an exploded view of a proximal portion of the electrosurgical probe.

FIG. 5 illustrates the electrical connections 250 within handle 204 for coupling electrode terminals 104 and return electrode 112 to the power supply 28. As shown, a plurality of wires 252 extend through shaft 100 to couple terminals 104 to a plurality of pins 254, which are plugged into a connector block 256 for coupling to a connecting cable 22 (FIG. 1). Similarly, return electrode 112 is coupled to connector block 256 via a wire 258 and a pin 260.

According to the present invention, the probe 90 further includes an identification element that is characteristic of the particular electrode assembly so that the same power supply 28 can be used for different electrosurgical operations. In one embodiment, for example, the probe 90 includes a voltage reduction element or a voltage reduction circuit for reducing the voltage applied between the electrode terminals 104 and the return electrode 112. The voltage reduction element serves to reduce the voltage applied by the power supply so that the voltage between the electrode terminals and the return electrode is low enough to avoid excessive power dissipation into the electrically conducting medium and/or ablation of the soft tissue at the target site. The voltage reduction element primarily allows the electrosurgical probe 90 to be compatible with other ArthroCare generators that are adapted to apply higher voltages for ablation or vaporization of tissue. For contraction of tissue, for example, the voltage reduction element will serve to reduce a voltage of about 100 to 135 volts rms (which is a setting of 1 on the ArthroCare Models 970, 980 and 2000 Generators) to about 45 to 60 volts rms, which is a suitable voltage for contraction of tissue without ablation (e.g., molecular dissociation) of the tissue.

Of course, for some procedures, the probe will typically not require a voltage reduction element. Alternatively, the probe may include a voltage increasing element or circuit, if desired.

In the representative embodiment, the voltage reduction element is a dropping capacitor 262 which has first leg 264 coupled to the return electrode wire 258 and a second leg 266 coupled to connector block 256. Of course, the capacitor may be located in other places within the system, such as is in, or distributed along the length of: (1) the cable; (2) in the generator; (3) in the connector, etc. In addition, it will be recognized that other voltage reduction elements, such as diodes, transistors, inductors, resistors, capacitors or combinations thereof, may be used in conjunction with the present invention. For example, the probe 90 may include a coded resistor (not shown) that is constructed to lower the voltage applied between return electrode 112 and electrode terminals 104 to a suitable level for contraction of tissue. In addition, electrical circuits may be employed for this purpose.

Alternatively or additionally, the cable 22 that couples the power supply 10 to the probe 90 may be used as a voltage reduction element. The cable has an inherent capacitance that can be used to reduce the power supply voltage if the cable is placed into the electrical circuit between the power supply, the electrode terminals and the return electrode. In this embodiment, the cable 22 may be used alone, or in combination with one of the voltage reduction elements discussed above, e.g., a capacitor.

Further, it should be noted that the present invention can be used with a power supply that is adapted to apply a voltage within the selected range for treatment of tissue. In this embodiment, a voltage reduction element or circuitry may not be desired.

Figure 7A:
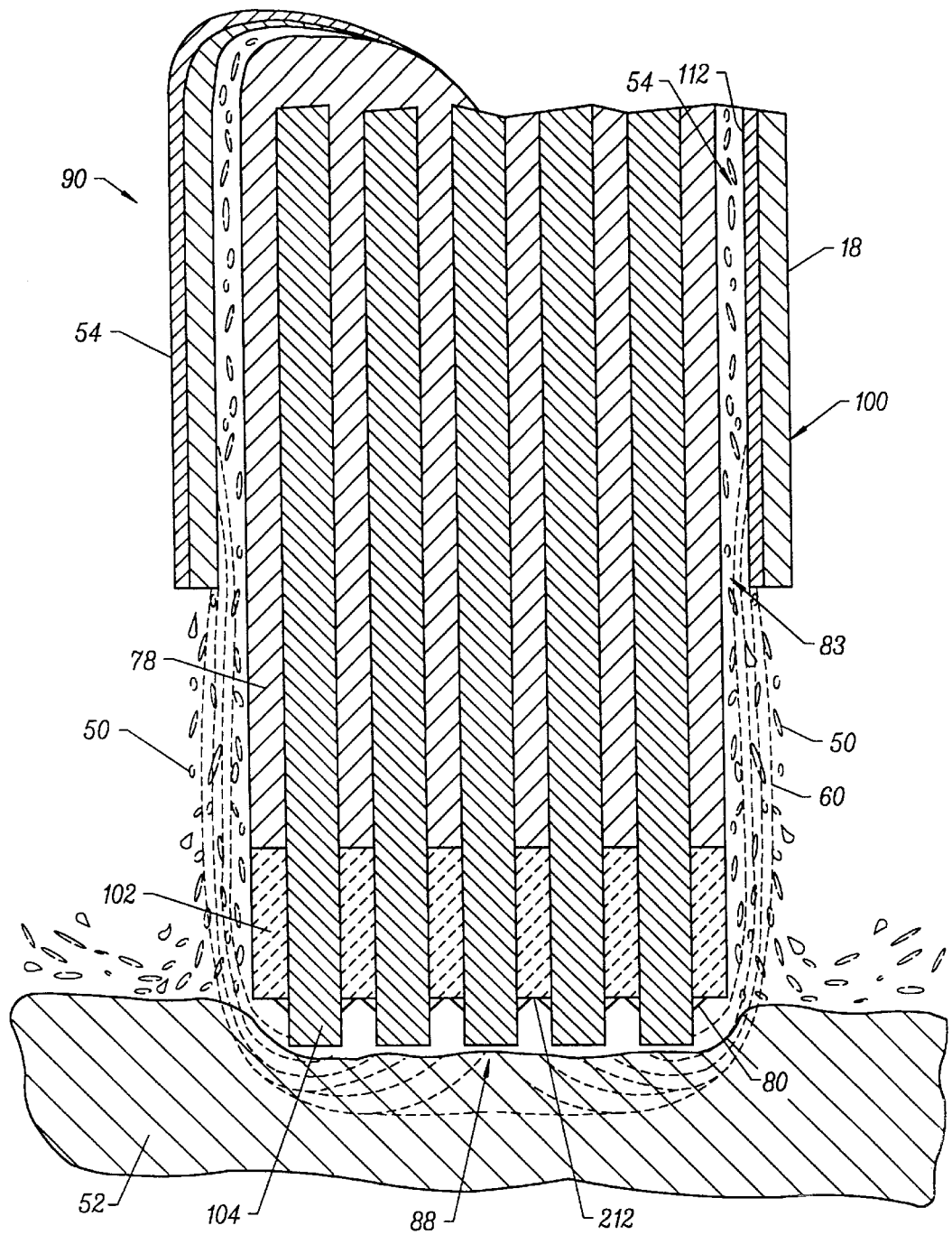
FIGS. 7A–7C are cross-sectional views of the distal portions of three different embodiments of an electrosurgical probe according to the present invention.
Figure 7B:
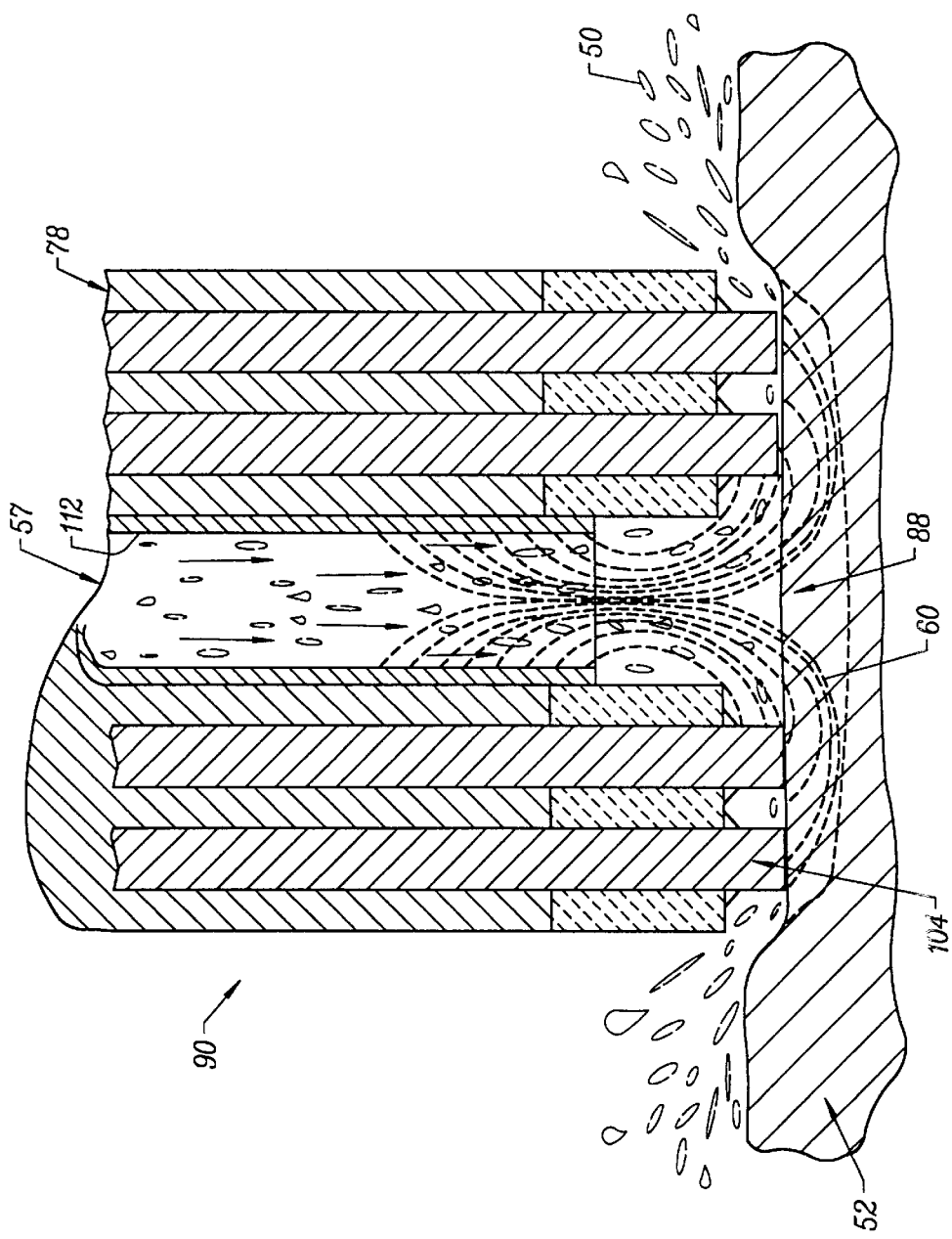
Figure 7C:
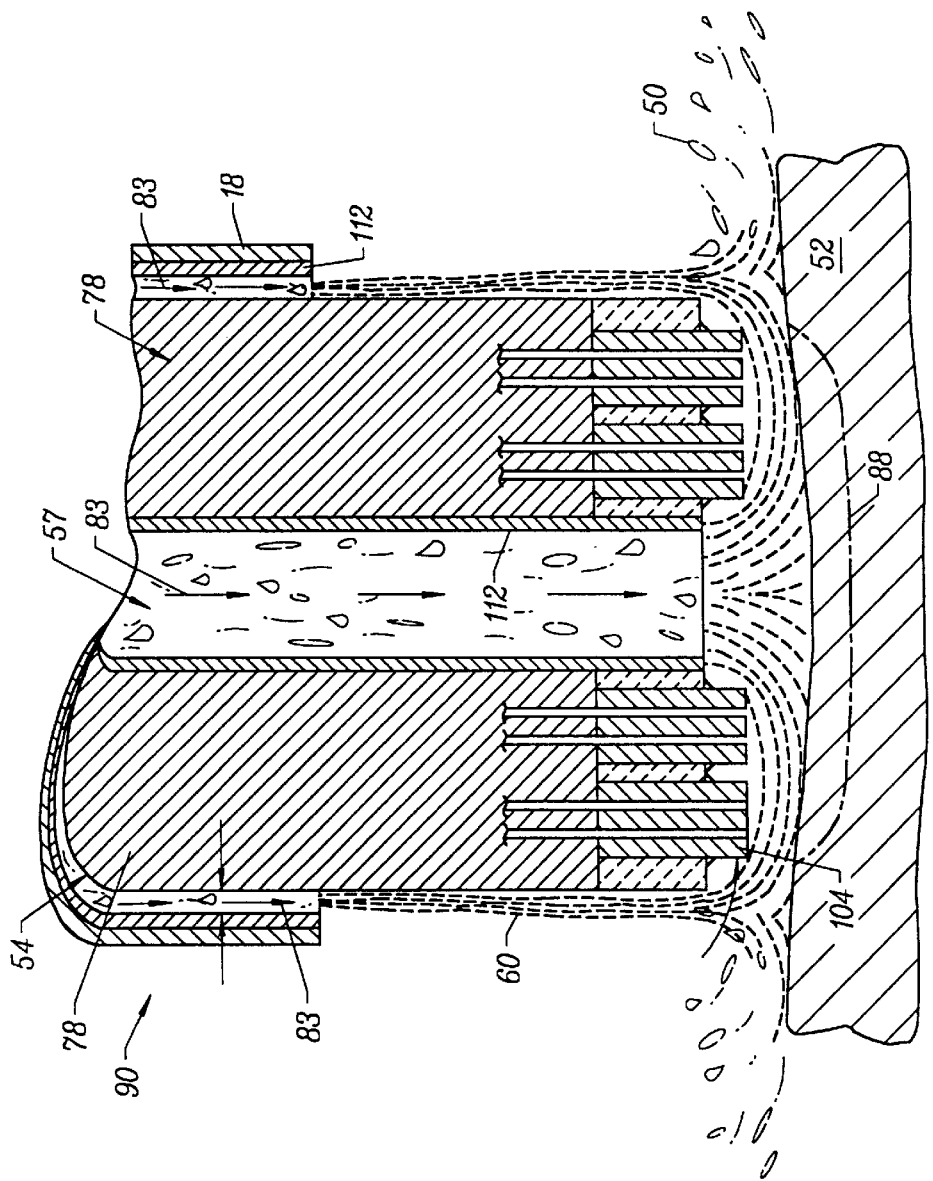

FIGS. 7A–7C schematically illustrate the distal portion of three different embodiments of probe 90 according to the present invention. As shown in 7A, electrode terminals 104 are anchored in a support matrix 102 of suitable insulating material (e.g., ceramic or glass material, such as alumina, silicon nitride zirconia and the like) which could be formed at the time of manufacture in a flat, hemispherical or other shape according to the requirements of a particular procedure. The preferred support matrix material is alumina, available from Kyocera Industrial Ceramics Corporation, Elkgrove, Ill., because of its high thermal conductivity, good thermal shock resistance, good electrically insulative properties, high flexural modulus, resistance to carbon tracking, biocompatibility, and high melting point. The support matrix 102 is adhesively joined to a tubular support member 78 that extends most or all of the distance between matrix 102 and the proximal end of probe 90. Tubular member 78 preferably comprises an electrically insulating material, such as an epoxy or silicone-based material.

In a preferred construction technique, electrode terminals 104 extend through pre-formed openings in the support matrix 102 so that they protrude above tissue treatment surface 212 by the desired distance. The electrodes are then bonded to the tissue treatment surface 212 of support matrix 102, typically by an inorganic sealing material 80. Sealing material 80 is selected to provide effective electrical insulation, and good adhesion to both the alumina matrix 102 and the electrode terminals (e.g., titanium, tungsten, molybdenum, platinum, etc.). Sealing material 80 additionally should have a compatible thermal expansion coefficient and a melting point well below that of the metal electrode terminals and the ceramic support matrix, typically being a glass or glass ceramic.

In the embodiment shown in FIG. 7A, return electrode 112 comprises an annular member positioned around the exterior of shaft 100 of probe 90. Return electrode 90 may fully or partially circumscribe tubular support member 78 to form an annular gap 54 therebetween for flow of electrically conducting fluid 50 therethrough, as discussed below. Gap 54 preferably has a width in the range of 0.1 mm to 4 mm. Alternatively, probe may include a plurality of longitudinal ribs between support member 78 and return electrode 112 to form a plurality of fluid lumens extending along the perimeter of shaft 100. In this embodiment, the plurality of lumens will extend to a plurality of openings.

Return electrode 112 is disposed within an electrically insulative jacket 18, which is typically formed as one or more electrically insulative sheaths or coatings, such as polytetrafluoroethylene, polyamide, and the like. The provision of the electrically insulative jacket 18 over return electrode 112 prevents direct electrical contact between return electrode 112 and any adjacent body structure. Such direct electrical contact between a body structure (e.g., tendon) and an exposed electrode member 112 could result in unwanted heating and necrosis of the structure at the point of contact causing necrosis.

As shown in FIG. 7A, return electrode 112 is not directly connected to electrode terminals 104. To complete this current path so that terminals 104 are electrically connected to return electrode 112, electrically conducting fluid 50 (e.g., isotonic saline) is caused to flow along fluid path(s) 83. Fluid path 83 is formed by annular gap 54 between outer return electrode 112 and tubular support member 78. The electrically conducting fluid 50 flowing through fluid path 83 provides a pathway for electrical current flow between electrode terminals 104 and return electrode 112, as illustrated by the current flux lines 60 in FIG. 6A. When a voltage difference is applied between electrode terminals 104 and return electrode 112, high electric field intensities will be generated at the distal tips of terminals 104 with current flow from terminals 104 through the target tissue to the return electrode, the high electric field intensities causing ablation of tissue 52 in zone 88.

FIG. 7B illustrates another alternative embodiment of electrosurgical probe 90 which has a return electrode 112 positioned within tubular member 78. Return electrode 112 is preferably a tubular member defining an inner lumen 57 for allowing electrically conducting fluid 50 (e.g., isotonic saline) to flow therethrough in electrical contact with return electrode 112. In this embodiment, a voltage difference is applied between electrode terminals 104 and return electrode 112 resulting in electrical current flow through the electrically conducting fluid 50 as shown by current flux lines 60 (FIG. 3). As a result of the applied voltage difference and concomitant high electric field intensities at the tips of electrode terminals 104, tissue 52 becomes ablated or transected in zone 88.

FIG. 7C illustrates another embodiment of probe 90 that is a combination of the embodiments in FIGS. 7A and 7B. As shown, this probe includes both an inner lumen 57 and an outer gap or plurality of outer lumens 54 for flow of electrically conductive fluid. In this embodiment, the return electrode 112 may be positioned within tubular member 78 as in FIG. 7B, outside of tubular member 78 as in FIG. 7A, or in both locations.

Figure 9:
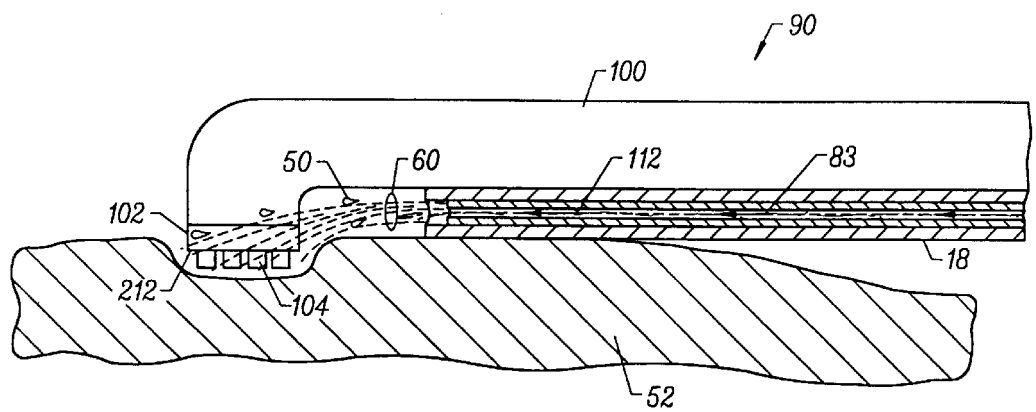
FIG. 9 illustrates an electrosurgical probe with a 90° distal bend and a lateral fluid lumen.

FIG. 9 illustrates another embodiment of probe 90 where the distal portion of shaft 100 is bent so that electrode terminals extend transversely to the shaft. Preferably, the distal portion of shaft 100 is perpendicular to the rest of the shaft so that tissue treatment surface 212 is generally parallel to the shaft axis. In this embodiment, return electrode 112 is mounted to the outer surface of shaft 100 and is covered with an electrically insulating jacket 18. The electrically conducting fluid 50 flows along flow path 83 through return electrode 112 and exits the distal end of electrode 112 at a point proximal of tissue treatment surface 212. The fluid is directed exterior of shaft to surface 212 to create a return current path from electrode terminals 104, through the fluid 50, to return electrode 12, as shown by current flux lines 60.

Figure 10:
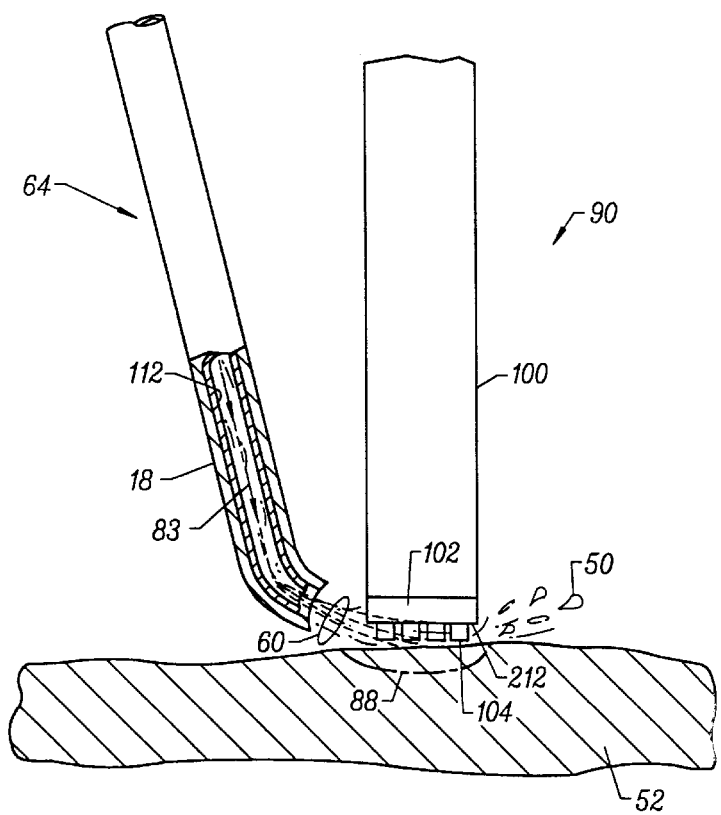
FIG. 10 illustrates an electrosurgical system with a separate fluid delivery instrument according to the present invention.

FIG. 10 illustrates another embodiment of the invention where electrosurgical system 11 further includes a fluid supply instrument 64 for supplying electrically conducting fluid 50 between electrode terminals 104 and return electrode 112. Fluid supply instrument 64 comprises an inner tubular member or return electrode 112 surrounded by an electrically insulating jacket 18. Return electrode 112 defines an inner passage 83 for flow of fluid 50. As shown in FIG. 8, the distal portion of instrument 64 is preferably bent so that fluid 50 is discharged at an angle with respect to instrument 64. This allows the surgical team to position fluid supply instrument 64 adjacent tissue treatment surface 212 with the proximal portion of supply instrument 64 oriented at a similar angle to probe 90.

Figure 8A:
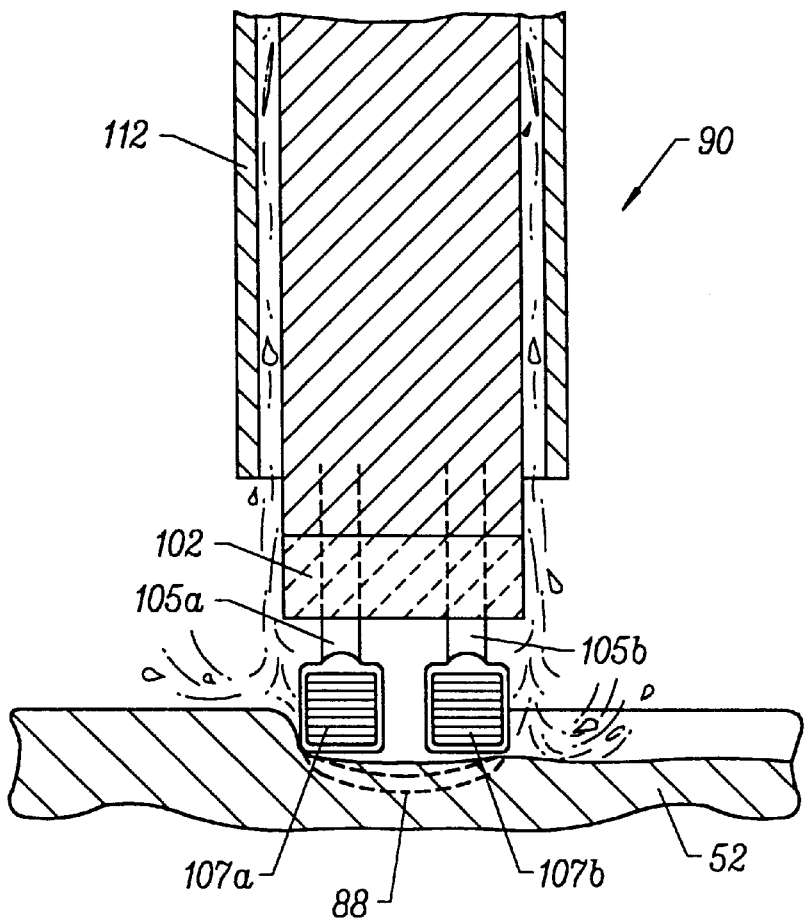
FIGS. 8A and 8B are cross-sectional and end views, respectively, of yet another electrosurgical probe incorporating flattened electrode terminals particularly useful for cutting tissue.
Figure 8B:
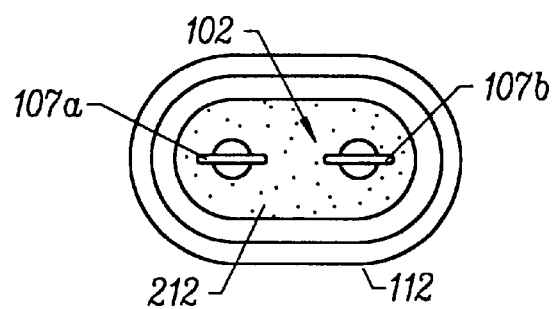

The present invention is not limited to an electrode array disposed on a relatively planar surface at the distal tip of probe 90, as described above. Referring to FIGS. 8A and 8B, an alternative probe 90 includes a pair of electrodes 105a, 105b mounted to the distal end of shaft 100. Electrodes 105a, 105b are electrically connected to power supply as described above and preferably have tips 107a, 107b with a screwdriver shape. The screwdriver shape provides a greater amount of "edges" to electrodes 105a, 105b, to increase the electric field intensity and current density at the edges and thereby improve the cutting ability as well as the ability to limit bleeding from the incised tissue (i.e., hemostasis).

Figure 11A:
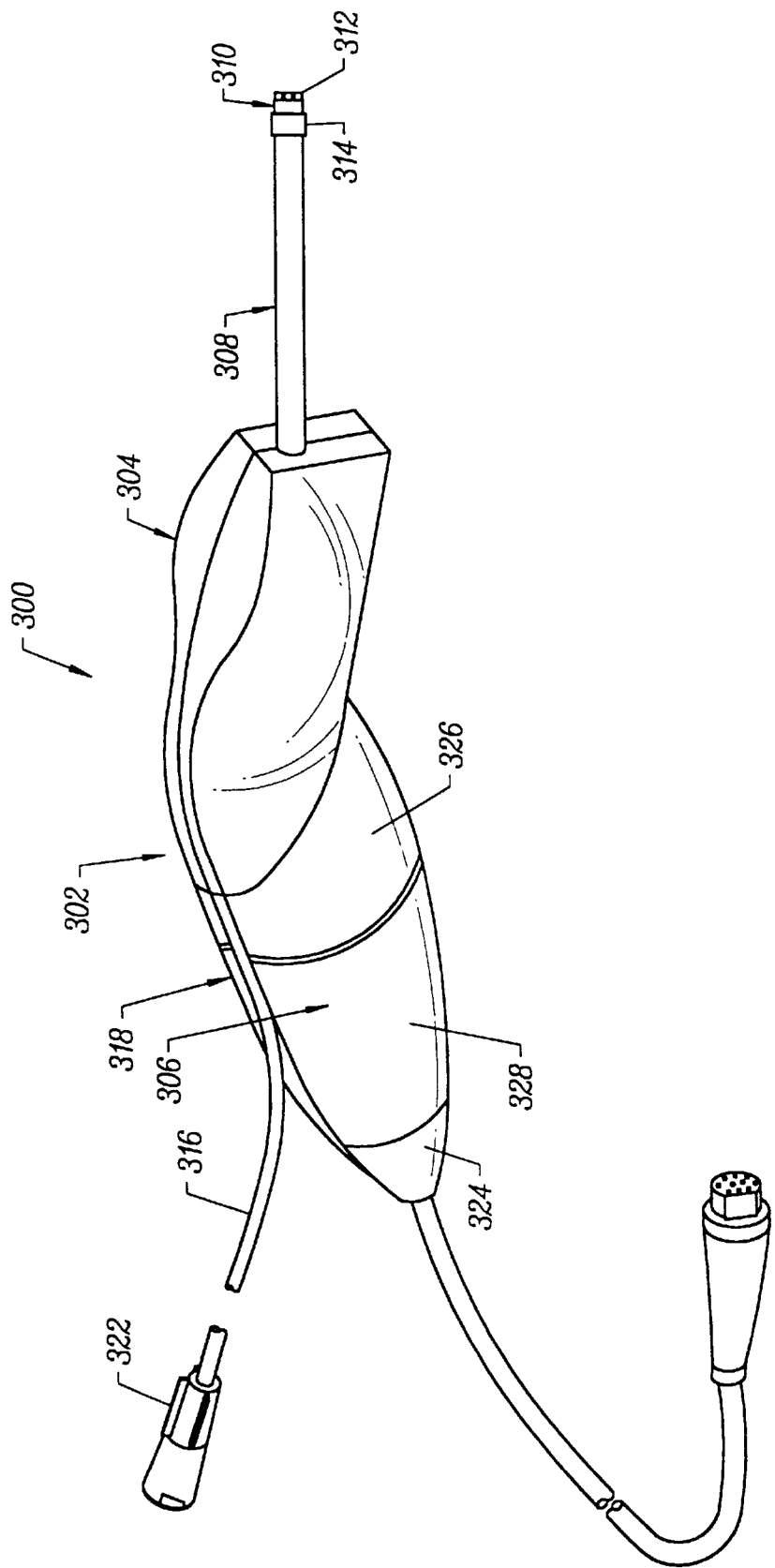
FIGS. 11A and 11B are perspective and end views, respectively, of an electrosurgical probe particularly useful for forming holes or channels in tissue, such as a commissurotomy of a calcified valve.
Figure 11B:
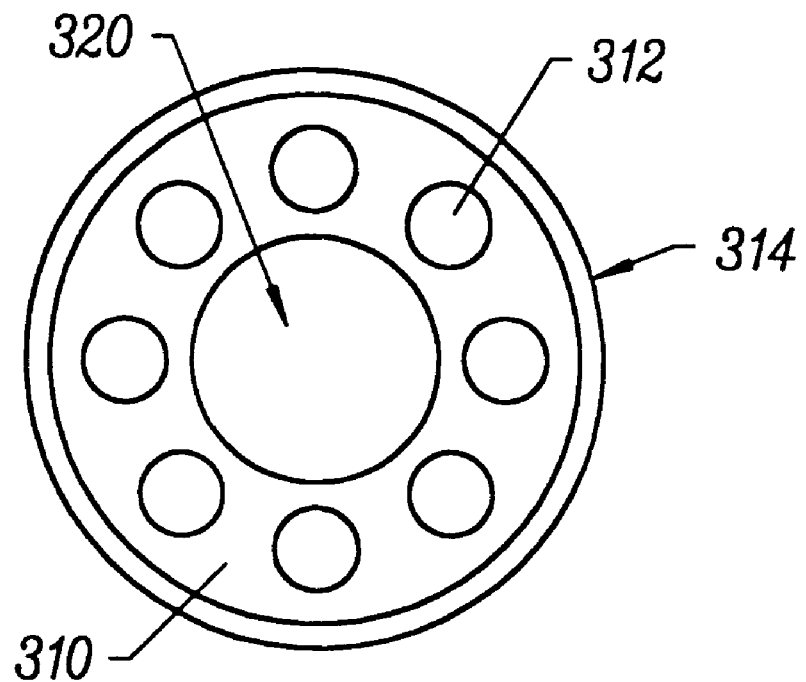

Referring now to FIGS. 11A and 11B, an exemplary electrosurgical probe 300 will now be described for use in calcified deposits and separating the adherent thickened leaflets of a stenotic heart valve. Probe 300 may be particularly useful for performing a commisurotomy in a heart valve (discussed in more detail below in reference to FIG. 19B). As shown, probe 300 comprises a handle 302, which preferably comprises a disposable distal portion 304 removably coupled to a proximal reusable portion 306, and an elongate shaft 308 extending from distal portion 304 of handle 302. Shaft 308 is also disposable, and is coupled to distal portion 304 of handle 302. The proximal and distal portions of handle 302 typically comprise a plastic material that is easily molded into a suitable shape for handling by the surgeon. Handle 302 defines an inner cavity (not shown) that houses the electrical connections (also not shown), and provides a suitable interface for connection to power supply 28 (FIG. 1). In the exemplary embodiment, the proximal portion of handle 302 is constructed so that it can be re-used by sterilizing handle 302 between surgical procedures. However, it should be understood that both the proximal and distal portions of the handle may be reusable, or both of these handle portions may be disposable, if desired.

Shaft 308 may be sized to provide either open-chest or endoscopic access to the thoracic cavity, preferably through an intercostal space or similar percutaneous penetration in the patient. Accordingly, shaft 308 preferably has a length in the range of about 4 to 25 cm and a diameter less than 10 cm. In the exemplary embodiment, shaft 308 is also preferably sized for ablating tissue containing calcified deposits or separating adherent valve leaflets and, therefore, will have a diameter less than 5 mm, preferably less than about 3 mm. Alternatively, shaft 308 may have a distal portion that is smaller than the rest of shaft for performing such procedures. As shown in FIG. 11A, shaft 308 includes an electrically insulating electrode support member 310 extending from its distal end (usually about 0.5 to 20 mm) to provide support for one or more electrically isolated electrode terminal(s) 312. Alternatively, electrode support member 310 may be recessed from the distal end of shaft 308 to help confine the electrically conductive fluid around the electrode terminals 312 during the surgical procedure, as discussed above.

In the embodiment shown in FIGS. 11A and 11B, probe 300 includes an annular return electrode 314 for completing the current path between electrode terminals 12 and power supply 28. Return electrode 314 is spaced proximally from electrode terminal(s) 312 a sufficient distance to avoid arcing therebetween. In addition, return electrode 314 is positioned such that, when electrode terminal(s) 312 are brought adjacent a tissue structure, return electrode 314 is spaced away from the tissue structure so that the tissue structure cannot, at least by itself, complete the current flow path between electrode terminal(s) 312 and return electrode 314.

Similar to previous embodiments, probe 300 includes a fluid tube 316 for delivering electrically conductive fluid to the target site. Fluid tube 316 is sized to extend through a groove 318 in handle 302 and through an inner cavity (not shown) in shaft 308 to a distal opening 320 (FIG. 11B) located adjacent electrode support member 310. Fluid tube 315 preferably extends all the way through the inner cavity to opening 320 to eliminate any possible fluid ingress into the cavity. As shown in FIG. 11A, fluid tube 316 includes a proximal connector 322 for coupling to an electrically conductive fluid source (see FIG. 1). Probe 300 will also include a valve or equivalent structure for controlling the flow rate of the electrically conducting fluid to the target site. In the representative embodiment, handle 302 comprises a main body 324, 326 and a rotatable sleeve 328 for controlling fluid flow through tube 316. Rotation of sleeve 328 crimps tube 316 to limit or complete shut off flow therethrough. Of course, this fluid control may be provided by a variety of other input and valve devices, such as switches, buttons, etc.

In alternative embodiments, the fluid path may be directly formed in probe 300 by, for example, a central inner lumen or an annular gap (not shown) within the handle and the shaft. This inner lumen may be formed near the perimeter of the probe 300 such that the electrically conducting fluid tends to flow radially inward towards the target site, or it may be formed towards the center of probe 300 so that the fluid flows radially outward. In addition, the electrically conducting fluid may be delivered from a fluid delivery element (not shown) that is separate from probe 300.

Referring to FIG. 11B, electrically isolated electrode terminals 312 are circumferentially spaced around fluid opening 320 at the tissue treatment surface of electrode support member 306. In the representative embodiment, the tissue treatment surface has a circular cross-sectional shape with a diameter of about 0.5 to 10 mm, usually less than 4 mm. The individual electrode terminals 312 have the dimensions described above, and preferably extend about 0.05 to 4.0 mm from the tissue treatment surface. Of course, the electrode terminals 312 may be substantially flush with the tissue treatment surface or the terminals may be recessed from this surface. For example, the electrode terminals 312 may be recessed by a distance from 0.01 mm to 2 mm, preferably 0.05 mm 5 to 1.0 mm. In one embodiment of the invention, the electrode terminals are axially adjustable relative to the tissue treatment surface so that the surgeon can adjust the distance between the surface and the electrode terminals.

Figure 12:
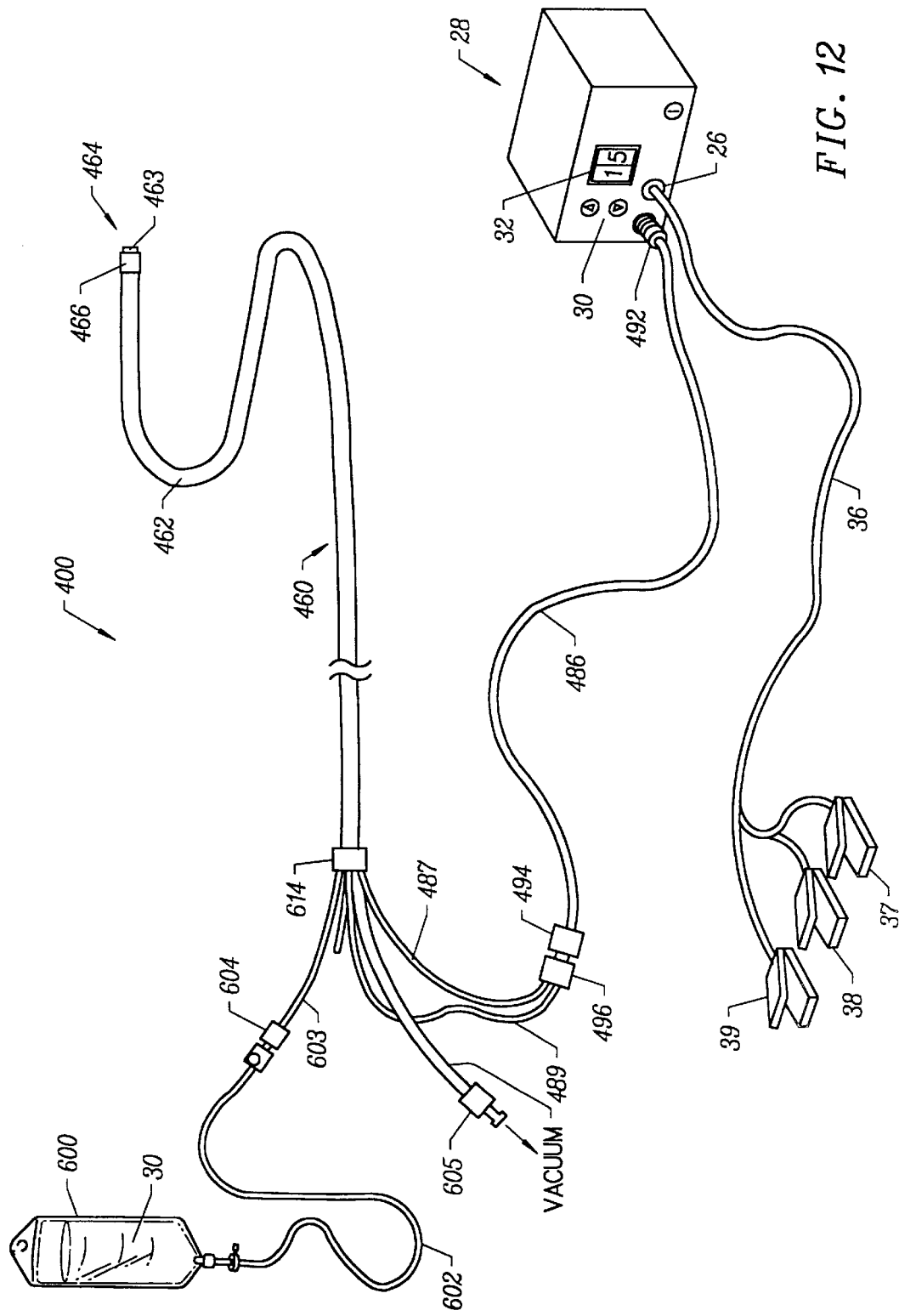
FIG. 12 is a perspective view of an electrosurgical catheter system for removing calcified deposits or other matter from a heart valve.

Referring to FIGS. 12–18, the electrosurgical device according to the present invention may also be configured as an elongate catheter system 400 including portions with sufficient flexibility to permit introduction into the body and to the heart through one or more vascular lumen(s). As shown in FIG. 12, a catheter system 400 generally comprises an electrosurgical catheter 460 connected to a power supply 28 by an interconnecting cable 486 for providing high frequency voltage to a target tissue site and an irrigant reservoir or source 600 for providing electrically conducting fluid to the target site. Catheter 460 generally comprises an elongate, flexible shaft body 462 including a tissue removing or ablating region 464 at the distal end of body 462. The proximal portion of catheter 460 includes a multi-lumen fitment 614 which provides for interconnections between lumens and electrical leads within catheter 460 and conduits and cables proximal to fitment 614. By way of example, a catheter electrical connector 496 is removably connected to a distal cable connector 494 which, in turn, is removably connectable to generator 28 through connector 492. One or more electrically conducting lead wires (not shown) within catheter 460 extend between one or more active electrodes 463 at tissue ablating region 464 and one or more corresponding electrical terminals (also not shown) in catheter connector 496 via active electrode cable branch 487. Similarly, one or more return electrodes 466 at tissue ablating region 464 are coupled to a return electrode cable branch 489 of catheter connector 496 by lead wires (not shown). Of course, a single cable branch (not shown) may be used for both active and return electrodes.

Catheter body 462 may include reinforcing fibers or braids (not shown) in the walls of at least the distal ablation region 464 of body 462 to provide responsive torque 30 control for rotation of electrode terminals during tissue engagement. This rigid portion of the catheter body 462 preferably extends only about 7 to 10 mm while the remainder of the catheter body 462 is flexible to provide good trackability during advancement and positioning of the electrodes adjacent target tissue.

Conductive fluid 30 is provided to tissue ablation region 464 of catheter 460 via a lumen (not shown in FIG. 12) within catheter 460. Fluid is supplied to lumen from the source along a conductive fluid supply line 602 and a conduit 603, which is coupled to the inner catheter lumen at multi-lumen fitment 614. The source of conductive fluid (e.g., isotonic saline) may be an irrigant pump system (not shown) or a gravity-driven supply, such as an irrigant reservoir 600 positioned several feet above the level of the patient and tissue ablating region 8. A control valve 604 may be positioned at the interface of fluid supply line 602 and conduit 603 to allow manual control of the flow rate of electrically conductive fluid 30. Alternatively, a metering pump or flow regulator may be used to precisely control the flow rate of the conductive fluid.

System 400 further includes an aspiration or vacuum system (not shown) to aspirate liquids and gases from the target site. The aspiration system will usually comprise a source of vacuum coupled to fitment 614 by a aspiration connector 605.

Figure 13:
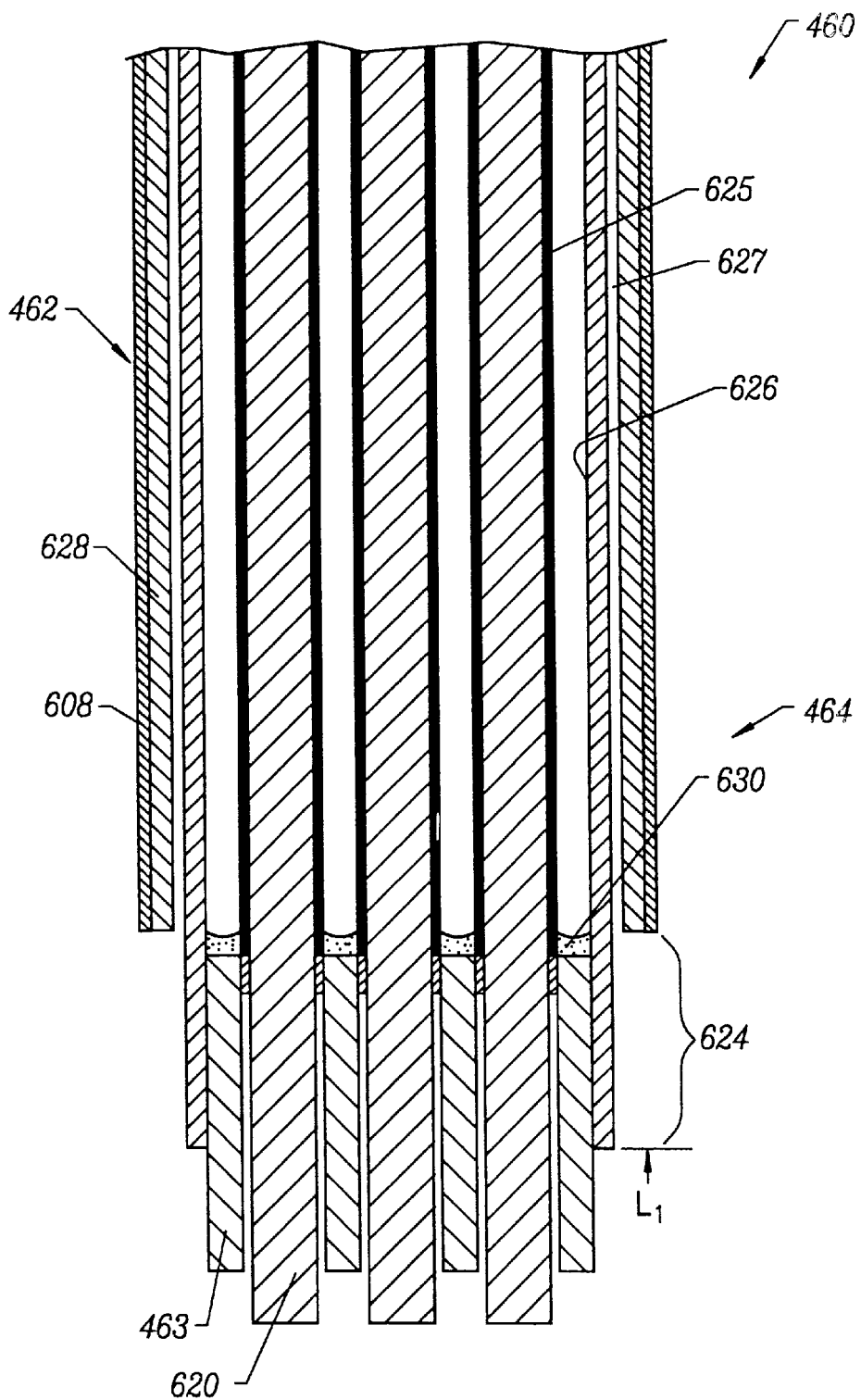
FIG. 13 illustrates the distal portion of an electrosurgical catheter for use with the system of FIG. 12.

FIGS. 13 and 14 illustrate the working end 464 of an electrosurgical catheter 460 constructed according to the principles of the present invention. As shown in FIG. 13, catheter 460 generally includes an elongated shaft 462 which may be flexible or rigid, and an electrode support member 620 coupled to the distal end of shaft 462. Electrode support member 620 extends from the distal end of shaft 462 (usually about 1 to 20 mm), and provides support for a plurality of electrically isolated electrode terminals 463. Electrode support member 620 and electrode terminals 463 are preferably secured to a tubular support member 626 within shaft 460 by adhesive 630.

The electrode terminals 463 may be constructed using round, square, rectangular or other shaped conductive metals. By way of example, the electrode terminal materials may be selected from the group including stainless steel, tungsten and its alloys, molybdenum and its alloys, titanium and its alloys, nickel-based alloys, as well as platinum and its alloys. Electrode support member 620 is preferably a ceramic, glass or glass/ceramic composition (e.g., aluminum oxide, titanium nitride). Alternatively, electrode support member 620 may include the use of high-temperature biocompatible plastics such as polyether-ether-keytone (PEEK) manufactured by Vitrex International Products, Inc. or polysulfone manufactured by GE Plastics. The adhesive 630 may, by way of example, be an epoxy (e.g., Master Bond EP42HT manufactured by Master Bond) or a silicone-based adhesive.

Figure 4:
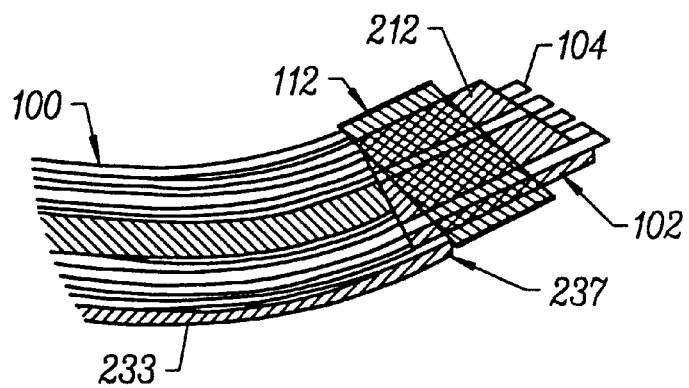
FIG. 4 is a cross sectional view of the electrosurgical probe of FIG. 1.
Figure 14A:
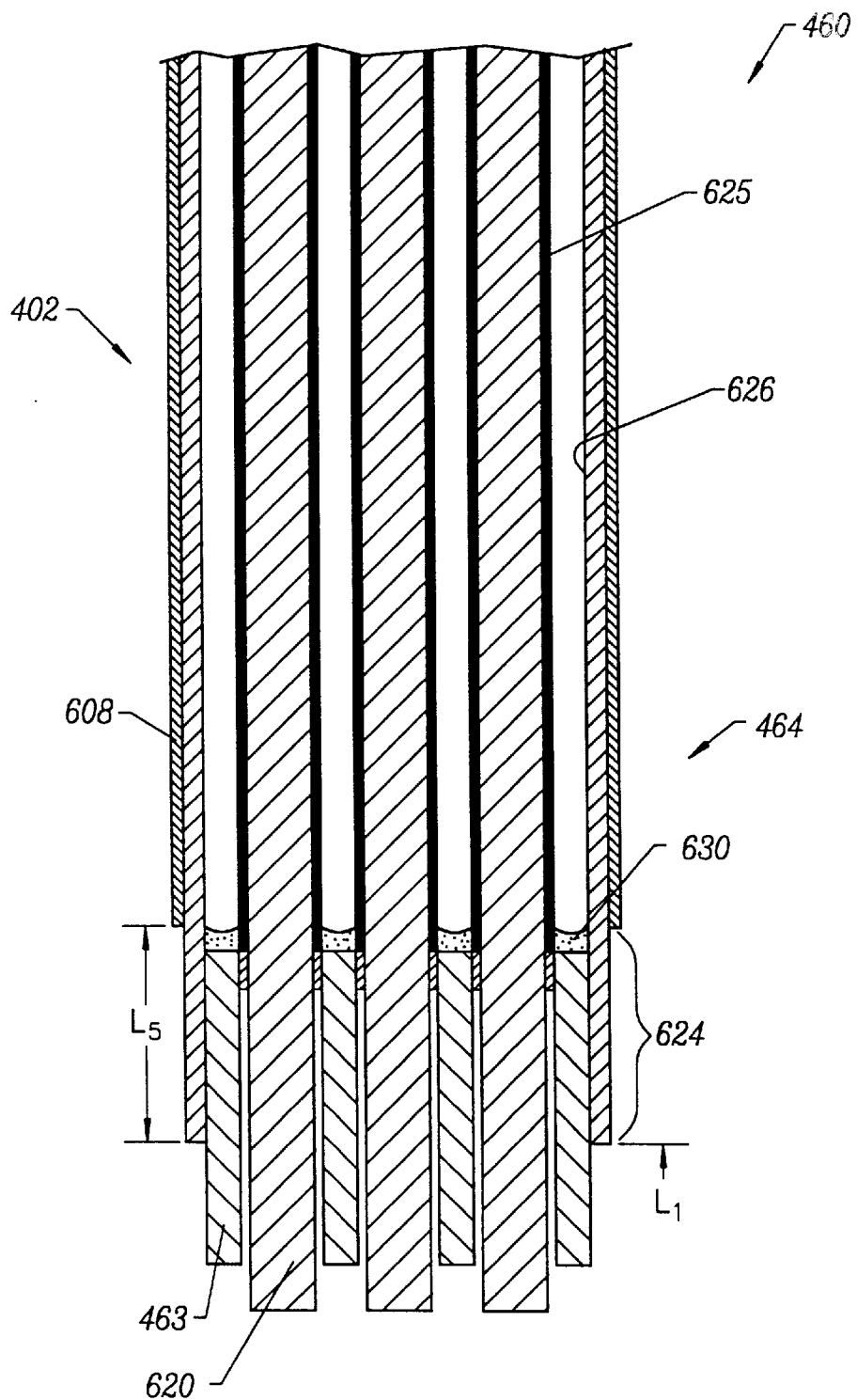
FIG. 14A and 14B are cross-sectional and end views, respectively of a distal portion of a second electrosurgical catheter according to the present invention.
Figure 14B:
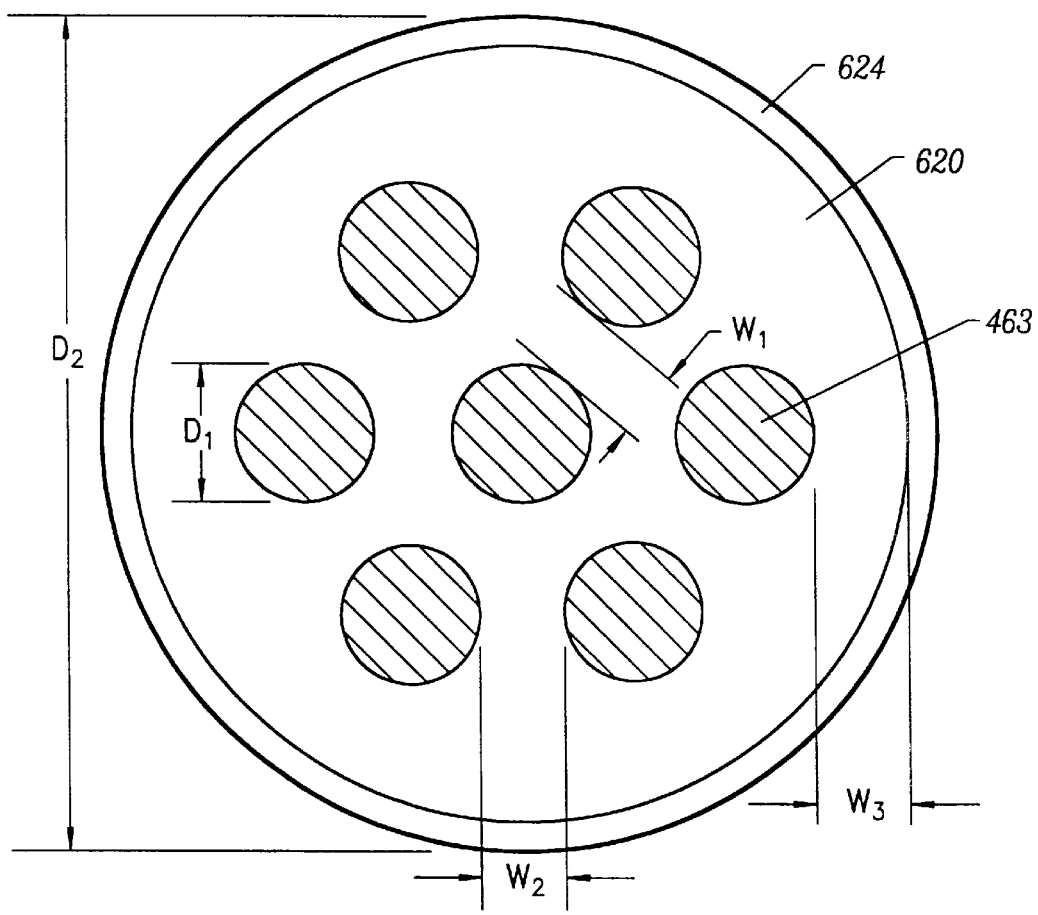

As shown in FIG. 14B, a total of 7 circular active electrodes or electrode terminals 463 are shown in a symmetrical pattern having an active electrode diameter, $D_1$ in the range from 0.05 mm to 1.5 mm, more preferably in the range from 0.1 mm to 0.75 mm. The interelectrode spacings, $W_1$ and $W_2$ are preferably in the range from 0.1 mm to 1.5 mm and more preferably in the range from 0.2 mm to 0.75 mm. The distance between the outer perimeter of the electrode terminal 463 and the perimeter of the electrode support member, $W_3$ is preferably in the range from 0.1 mm to 1.5 mm and more preferably in the range from 0.2 mm to 0.75 mm. The overall diameter, $D_2$ of the working end 464 of catheter body 462 is preferably in the range from 0.5 mm to 10 mm and more preferably in the range from 0.5 mm to 5 mm. As discussed above, the shape of the active electrodes may be round, square, triangular, hexagonal, rectangular, tubular, flat strip and the like and may be arranged in a circularly symmetric pattern as shown in FIG. 4 or may, by way of example, be arranged in a rectangular pattern, square pattern, or strip.

Catheter body 462 includes a tubular cannula 626 extending along body 462 radially outward from support member 620 and electrode terminals 463. The material for cannula 626 may be advantageously selected from a group of electrically conductive metals so that the cannula 626 functions as both a structural support member for the array of electrode terminals 463 as well as a return electrode 624. The support member 626 is connected to an electrical lead wire (not shown) at its proximal end within a connector housing (not shown) and continues via a suitable connector to power supply 28 to provide electrical continuity between one output pole of high frequency generator 28 and said return electrode 624. The cannula 626 may be selected from the group including stainless steel, copper-based alloys, titanium or its alloys, and nickel-based alloys. The thickness of the cannula 626 is preferably in the range from 0.08 mm to 1.0 mm and more preferably in the range from 0.05 mm to 0.4 mm.

As shown in FIGS. 13 and 14A, cannula 626 is covered with an electrically insulating sleeve 608 to protect the patient's body from the electric current. Electrically insulating sleeve 608 may be a coating (e.g., nylon) or heat shrinkable plastic (e.g., fluropolymer or polyester). As shown in FIG. 14A, the proximal portion of the cannula 626 is left exposed to function as the return electrode 624. The length of the return electrode 624, $L_5$ is preferably in the range from 1 mm to 30 mm and more preferably in the range from 2 mm to 20 mm. The spacing between the most distal portion of the return electrode 624 and the plane of the tissue treatment surface 622 of the electrode support member 620, $L_1$ is preferably in the range from 0.5 mm to 30 mm and more preferably in the range from 1 mm to 20 mm. The thickness of the electrically insulating sleeve 608 is preferably in the range from 0.01 mm to 0.5 mm and more preferably in the range from 0.02 mm to 0.2 mm.

In the embodiment shown in FIG. 13, the fluid path is formed in catheter by an inner lumen 627 or annular gap between the return electrode 624 and a second tubular support member 628 within shaft 460. This annular gap may be formed near the perimeter of the shaft 460 as shown in FIG. 13 such that the electrically conducting fluid tends to flow radially inward towards the target site, or it may be formed towards the center of shaft 460 (not shown) so that the fluid flows radially outward. In both of these embodiments, a fluid source (e.g., a bag of fluid elevated above the surgical site or having a pumping device), is coupled to catheter 460 via a fluid supply tube (not shown) that may or may not have a controllable valve.

In an alternative embodiment shown in FIG. 14A, the electrically conducting fluid is delivered from a fluid delivery element (not shown) that is separate from catheter 460. In arthroscopic surgery, for example, the body cavity will be flooded with isotonic saline and the catheter 460 will be introduced into this flooded cavity. Electrically conducting fluid will be continually resupplied to maintain the conduction path between return electrode 624 and electrode terminals 463.

Figure 15A:
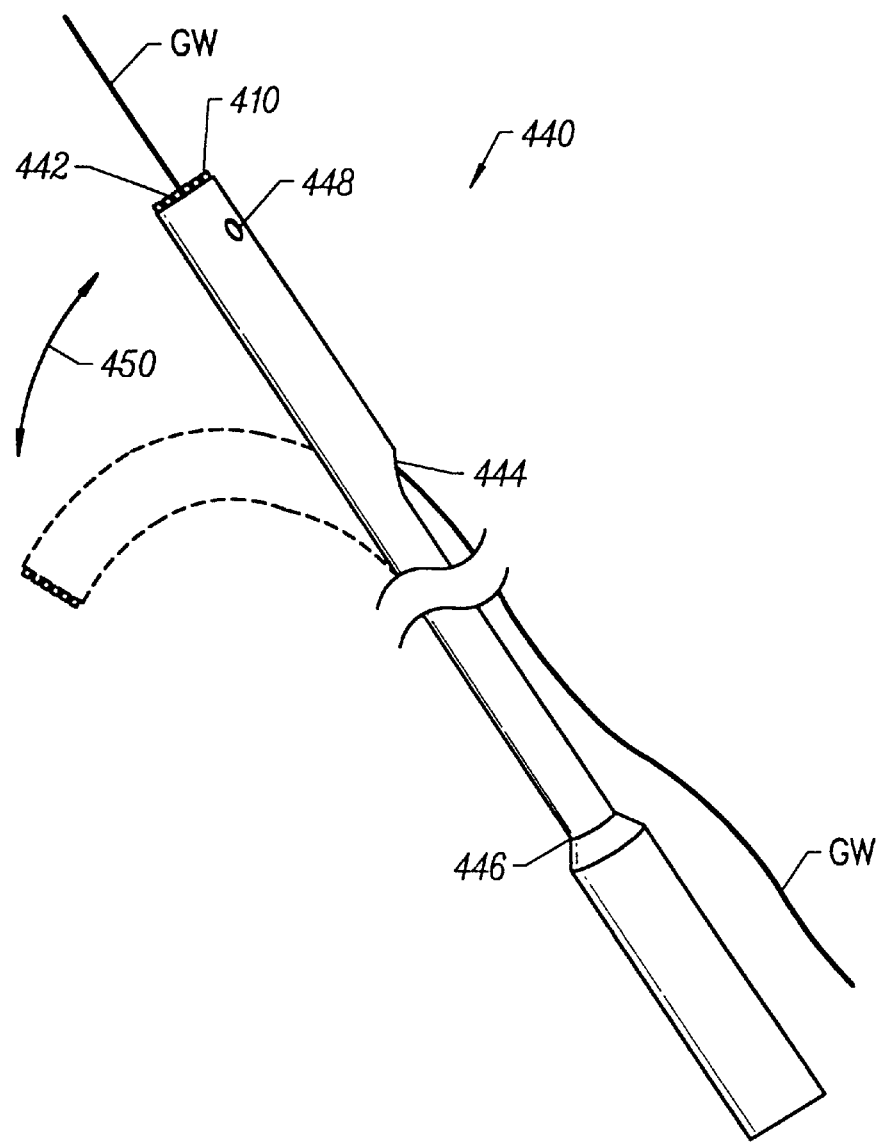
FIGS. 15A–15D show alternative embodiments of the present invention.

Referring to FIG. 15A, a further alternative embodiment of a catheter 440 will be described. The catheter 440 has isolated electrode terminals 410 located near a distal end of the catheter. The catheter 440 has a rapid-exchange design where the guidewire GW passes through a distal port 442 and exits through a proximal port 444 located closer to the distal port than the proximal end 446 of the catheter. The rapid-exchange design allows for the use of a shorter guidewire GW and facilitates the changing of catheters without repositioning of the guidewire. A fluid injection port 448 is provided near the distal end of the catheter to supply electrically conductive fluid to the electrode terminals 410 when desired. The catheter 440 may also contain push/pull wires that allow a user to manipulate the curvature of the distal end of the catheter as indicated by arrow 450. This facilitates the positioning of the electrode terminals 410 near a target site, creating a stearable catheter.

Figure 15B:
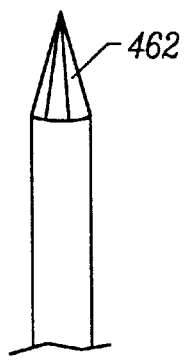
Figure 15C:
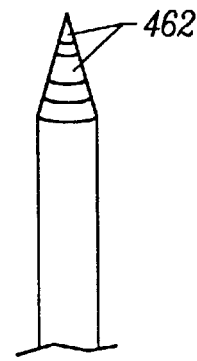
Figure 15D:
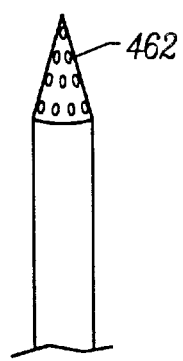

In certain procedures, a pointed tip 460 may be required on the distal end of a catheter or probe. This allows the user or surgeon to apply energy to a smaller region and shape the area being treated. It allows the same instrument to shape tissue but also puncture or cut material as needed. FIGS. 15B–15D show various embodiments of the tip 460 having multiple-electrodes 462. Alternatively, a single electrode may be used to apply energy to a confined region of target tissue.

Figure 16:
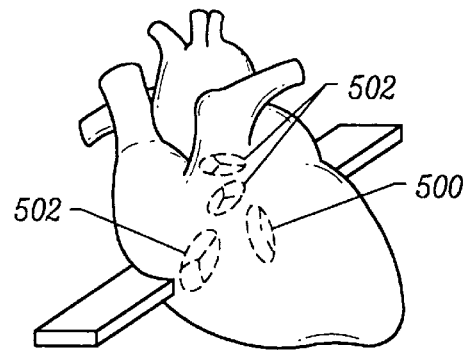
FIG. 16 is a schematic of the heart showing the location of various heart valves.
Figure 17A:
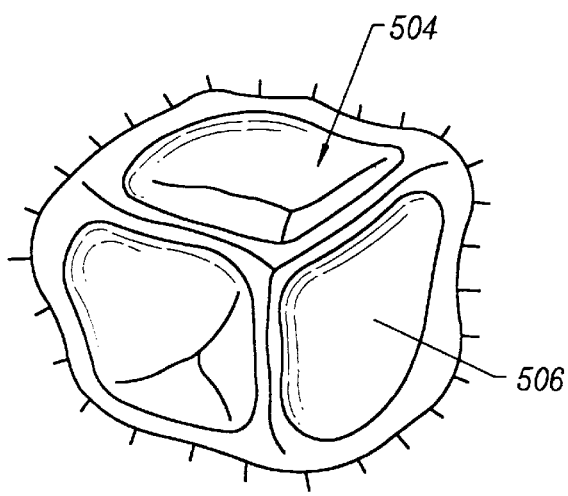
FIGS. 17A–17B are overhead and side views of a tricuspid valve.
Figure 17B:
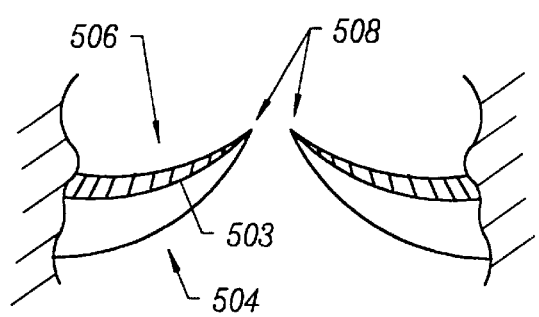

FIGS. 16–21 illustrate methods for treating cardiac tissue such as valve leaflets that are coated with calcified deposits or fibrotic tissue. FIG. 16 shows the location of various bicuspid and tricuspid valves 500 and 502 in the heart. In these procedures, the undesired calcified deposits or fibrotic tissue may be ablated or reduced to clear stenotic material and to restore tissue flexibility. Often, calcified deposits 503 (FIG. 17B) are hardened to and substantially fused to the cardiac tissue. This is particularly detrimental to the functionality of valve leaflets 504 (FIGS. 17A and 17B) which requires flexibility in the cusp area 506 to open and close (as indicated by arrows 508). Reduced flexibility decreases leaflet mobility and may cause valve closure problems and backflow leakage of blood or regurgitation. The present invention may be used for valve repair by debridement/decalcification, or in valve replacement procedures for calcific debridement.

Figure 18:
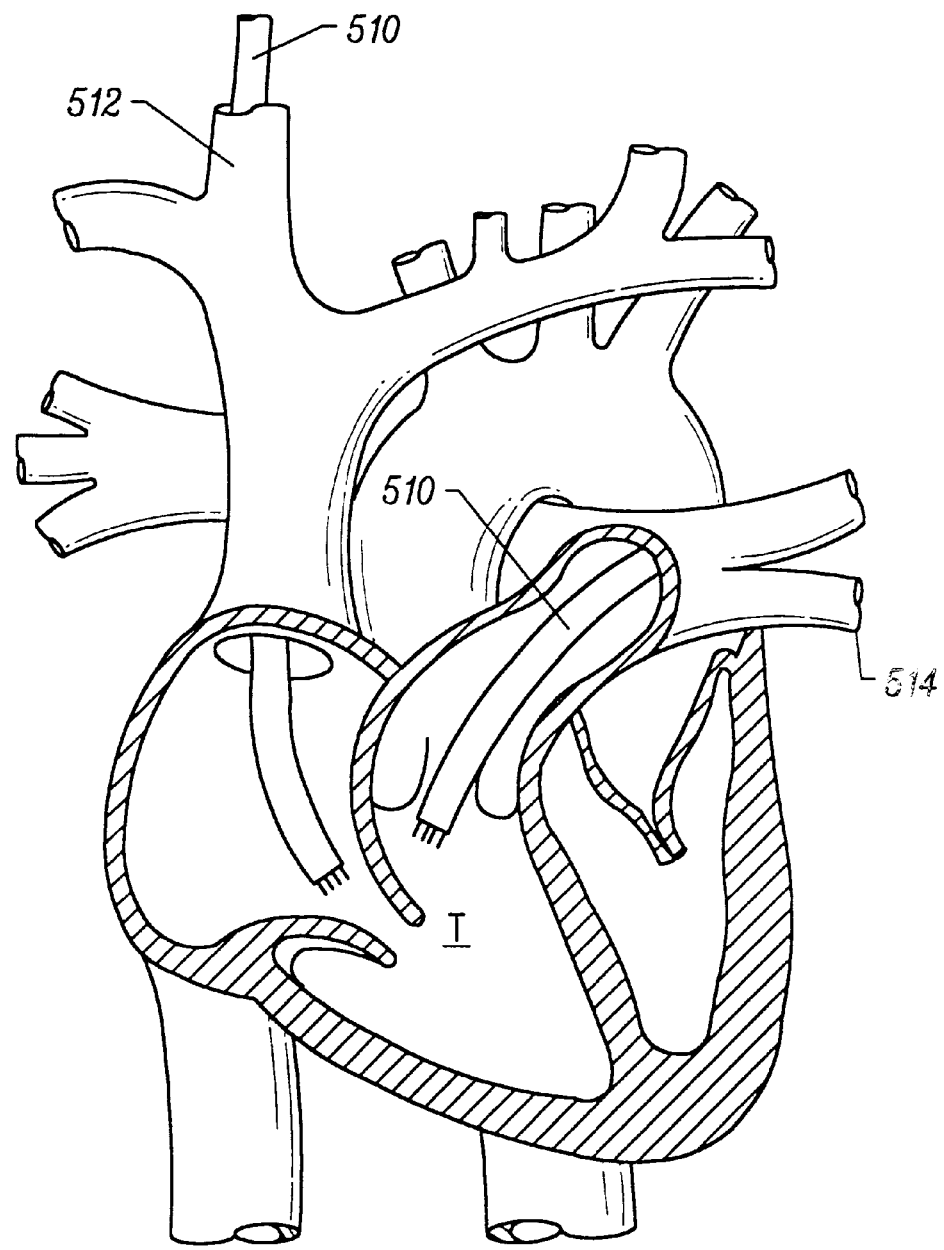
FIG. 18 is a partial cross-sectional view of the heart being treated by a device according to the present invention.

The present invention may be used in percutaneous, minimally invasive, or open surgery techniques to access a target site T in the heart. FIG. 18 shows a percutaneous-type treatment technique where an electrosurgical catheter 510 is introduced into the interior of the heart without a cardiac cut-down procedure. To gain access to the heart, the catheter 510 is typically inserted into the patient's vasculature through a large blood vessel such as the femoral artery or the right jugular vein 512, as well-described in the art. Alternatively, the surgeon may also attempt to enter the pulmonary trunk 514 to access the pulmonary semilunar valve 516.

Figure 19A:
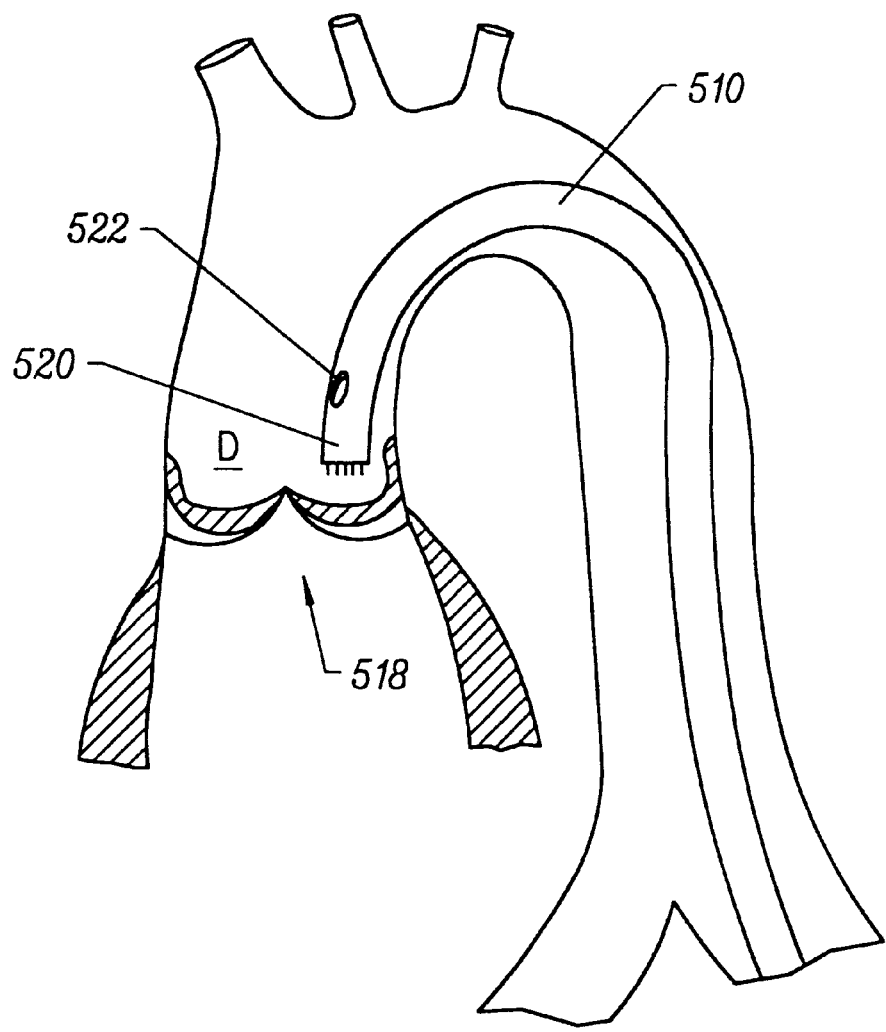
FIG. 19A shows a device of the present invention treating an aortic semilunar valve.

Once inserted into the heart, the catheter 510 (FIG. 19A) can be directed towards the target site T through endoscopic, fluoroscopic, ultrasonic, or other visualization methods. FIG. 19A shows the catheter 510 approaching the aortic semiluminar valve 518. During the procedure, conventional endoscopic or fluoroscopic imaging techniques may be utilized to allow the physician to view the relative locations of electrosurgical catheter 510 and the calcified deposits D which are to be removed from the 30 aortic valve leaflets. In the case of fluoroscopic visualization, the components of the electrosurgical catheter 510 are preferably either radio-opaque or marked with radio-opaque markers so that they will be visible by fluoroscopy. Visualization of any support equipment and the inferior surface of the leaflets may be further facilitated by injecting radiographic contrast solution into confined areas of the vasculature. Ultrasonic method may also be used to provide cross-sectional imaging of the target area. Known ultrasound imaging techniques are described in N. Bom and J. Roelandt, "Intravascular Ultrasound," (Kluwer Academic Publishers 1989) which contains a variety of articles detailing techniques, developments, and clinical perspectives on intravascular ultrasound procedures.

Aortic or mitral valve repair are preferably performed on patients only after cardiopulmonary bypass and cardioplegic arrest. However, the heart may be temporarily arrested, or slowed down, sufficiently to perform this procedure without bypass. Following cross-clamping of the aorta, aortic and mitral valves can be inspected for calcified deposits. Additional tools for manipulating and positioning the valve such as catheters with graspers and support backing may also be introduced near the valve leaflet. Decalcification is begun by positioning the catheter tip 520 within the vicinity of the calcified deposits D. Preferably, the catheter 510 has a source of conductive fluid such as isotonic saline as provided by port 522 on the catheter. This isotonic saline provides a conductive path between the active and return electrodes (in the bipolar modality) and the charged particles required for the cold ablation technique of the present invention. Alternatively, the catheter 510 may use some naturally occurring fluid such as blood or other body fluid that has electrolytic qualities sufficient for these purposes. The catheter 510 may be used to treat the valve leaflet by incising the atrial endothelium around the borders of the calcified bar and then working its way across the surface of the leaflet cusp 506.

During the course of treatment, it may be discovered that the calcium deposits D on the valve leaflets may extend onto adjacent areas of the heart, beyond the valvular annulus. This is particularly true when dealing with a calcified aortic or calcified mitral annulus. With its ability to remove tissue to a precise depth while minimizing necrosis of the underlying tissue, electrosurgical catheter 510 may also be directed to remove these deposits D from the heart. Additionally, it may occur during treatment that the valve is beyond repair and needs to be excised. The electrosurgical catheter 510 may be used to remove calcium deposits along the annulus of the valve to facilitate removal by scalpel or other cutting device. This may be necessary as the calcium formation is often quite hard and encapsulated with a fibrous sheath. To prevent calcium fragmentation and accidental damage to surrounding tissue, the catheter 510 can either vaporize the deposits or loosen it enough for a scalpel to remove the deposit without fragmentation.

Figure 19B:
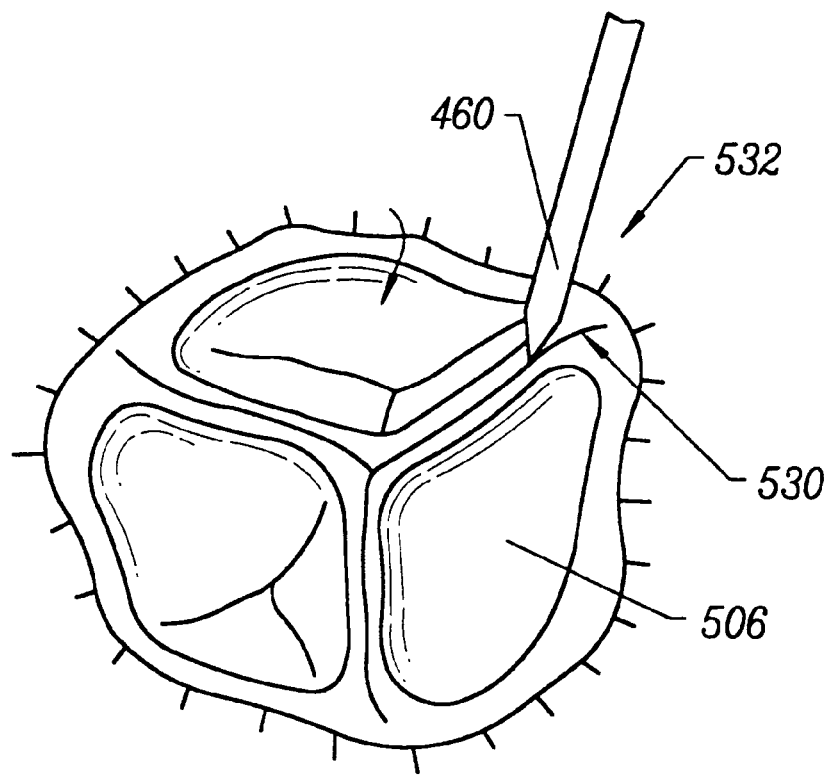
FIG. 19B shows a device of the present invention performing a commissurotomy.

In other procedures, the probe of the present invention may be used to perform a commissurotomy on the heart valve to separate valve leaflets that are calcified shut. As illustrated in FIG. 19B, a probe or catheter having a pointed end 460 is particularly suited for performing a commissurotomy on the commissures 530. The commissures 530 are the locations where the valve leaflets meet, particularly those area near the annulus 532 of the valve. The commissures 530 may become fused to each other due to the formation of scar tissue or other material due to rheumatic fever or other causes. The fusing of the leaflets at the commissures 530 narrows the opening that can be created by the valve, reducing blood flow from the heart. The precision cutting capability of tip 460 can be used to vaporize the undesired materials and facilitates the separation of the commissures 530 with minimal risk of creating fragments that may flow into the vasculature. The pointed tip 460 advantageously provides shaping and cutting capabilities in the same instrument.

Figure 20:
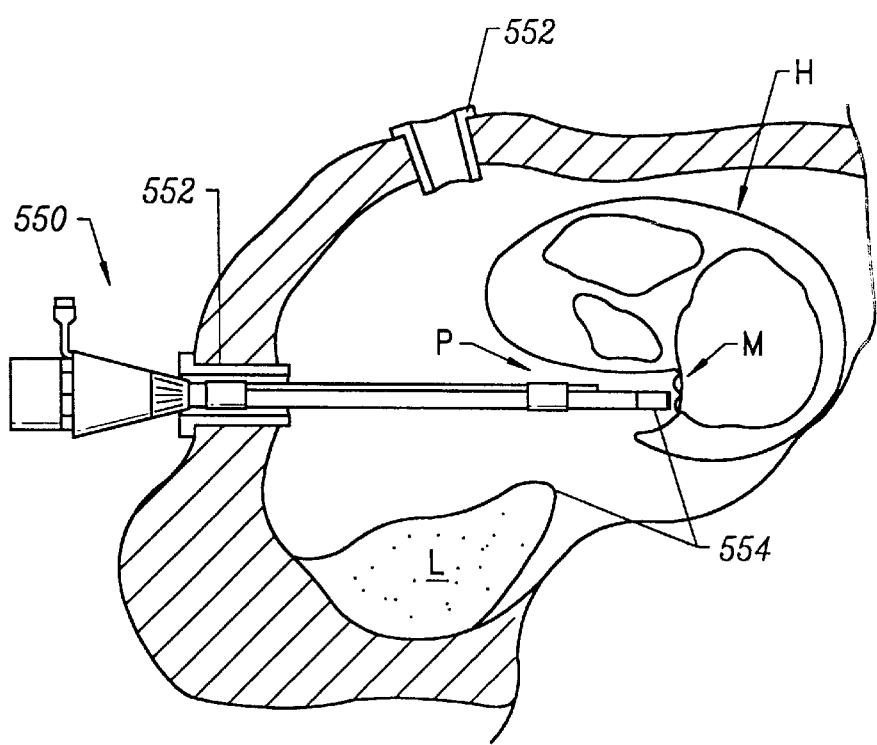
FIG. 20 shows a device of the present invention used in a port access procedure in the chest of a patient.

Referring to FIG. 20, an electrosurgical probe 550 of the present invention may be used in a minimally invasive, Port Accessu procedure. In these procedures, ports 552 are placed in the thoracic region of the patient, through percutaneous intercostal penetrations between the patient's ribs. One of the lungs L are typically deflated to provide access to the heart H. An internal penetration P is formed in the wall of the heart to gain access to interior regions. Further details of a suitable closed-chest, port access procedure may be found in U.S. Pat. No. 5,682,906 issued to Heartport, Inc. of Redwood City, Calif., the full disclosure of which is incorporated herein by reference. FIG. 17 shows the probe 550 approaching the mitral valve M for treatment.

Typically, these port access procedures are performed with the heart stopped, using techniques known in the art, and the patient placed on a heart-lung bypass machine. Alternatively, the patient's heart may remain beating, albeit preferably at a reduced rate. The heart may be momentarily substantially stopped or slowed in a predictable and reliable manner to facilitate the surgery by electrically stimulating the vagus nerve. This stimulation can be accomplished by gaining access to the vagus nerve in the neck or in the chest and then using a suitable device, e.g., a commercially available nerve stimulator or insulated pacing wires with distally exposed conductors connected to a current source, to briefly, e.g., for 1 to 5 seconds, apply electric energy to the vagus nerve. A 50 millihertz current may be used, but the present invention is not limited to any particular quantitative amount of electrical energy. The time of the stimulation and amount of current applied will vary according to the type of surgery and the nature of the task for which substantial stopping or slowing of the heart is desired. In any event, the normal sinuous rhythm of the heart is rapidly restored by natural forces once the stimulation is terminated. Thus, for repetitive tasks such as debridement of calcium deposits, the stimulation may be repeatedly applied for brief intervals during which time the task can be performed in less difficult conditions than would apply if the heart were beating in a normal manner. Additional details on the slowing of the heart can be found in U.S. Pat. No. 5,651,378 issued to CardioThoracic Systems, Inc. of Cupertino Calif., the full disclosure of which is incorporated herein by reference.

Figure 21A:
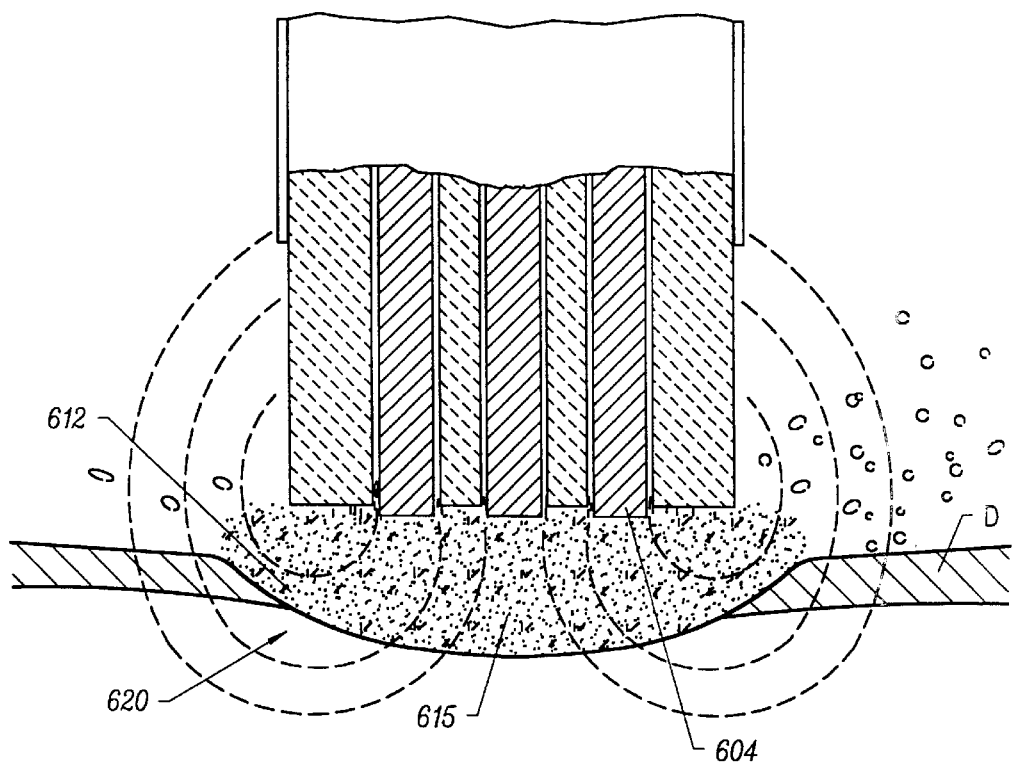
FIGS. 21A–21B illustrate a detailed view of the calcium removal procedure, illustrating ablation of tissue according to the present invention.
Figure 21B:
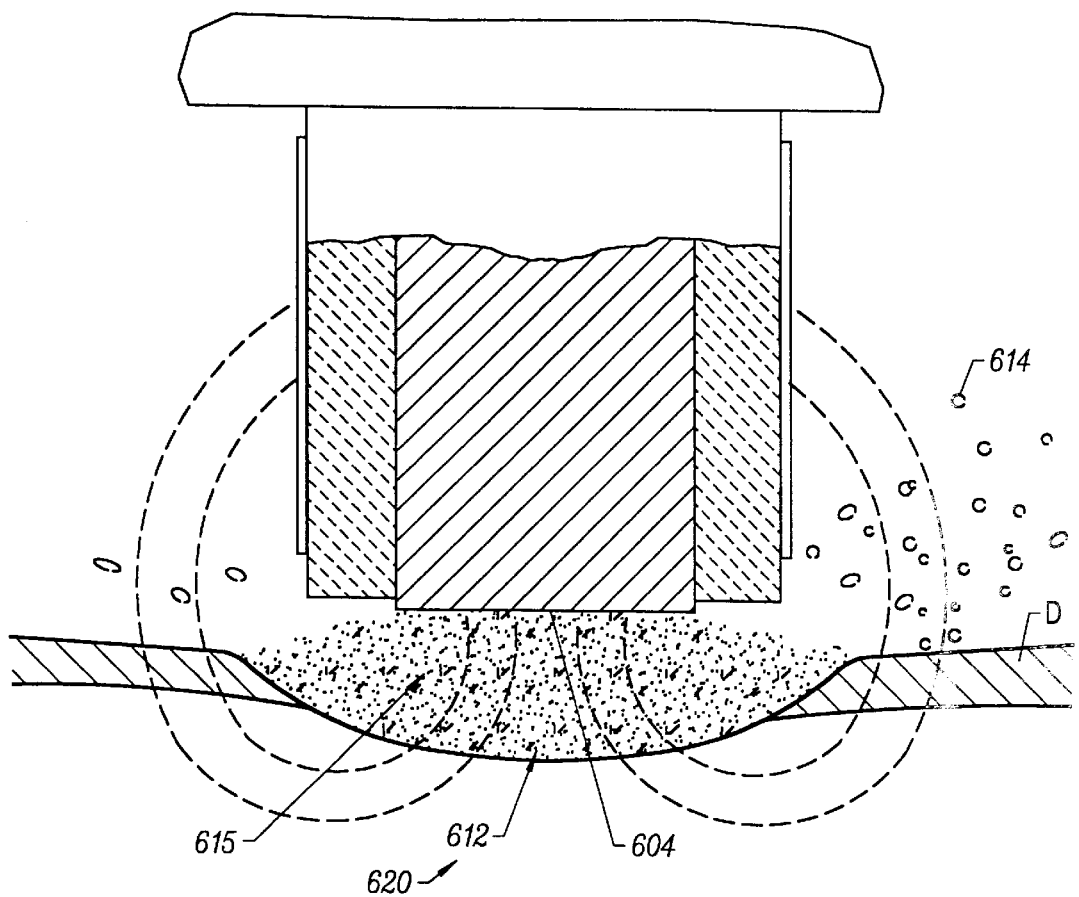

FIGS. 21A and 21B illustrate the removal of calcified material in more detail (FIG. 21B illustrates a single electrode). As shown, the high frequency voltage is sufficient to convert the electrically conductive fluid (not shown) between the calcium deposit D and electrode terminal(s) 604 into an ionized vapor layer 612 or plasma. As a result of the applied voltage difference between electrode terminal(s) 604 and the calcium deposit D (i.e., the voltage gradient across the plasma layer 612), charged particles 615 in the plasma (viz., electrons) are accelerated towards the tissue. At sufficiently high voltage differences, these charged particles 615 gain sufficient energy to cause dissociation of the molecular bonds within tissue structures. This molecular dissociation is accompanied by the volumetric removal (i.e., ablative sublimation) of tissue and the production of low molecular weight gases 614, such as oxygen, nitrogen, carbon dioxide, hydrogen and methane. The short range of the accelerated charged particles 615 within the tissue confines the molecular dissociation process to the surface layer to minimize damage and necrosis to the underlying tissue 620. As can be seen in the figures, the calcium deposit D is removed up to the layer of living tissue 620.

Other modifications and variations can be made to disclose embodiments without departing from the subject invention as defined in the following claims. For example, it should be noted that the invention is not limited to an electrode array comprising a plurality of electrode terminals. The invention could utilize a plurality of return electrodes, e.g., in a bipolar array or the like. In addition, the active and return electrodes may both be located on a distal tissue treatment surface adjacent to each other. The active and return electrodes may be located in active/return electrode pairs, or one or more return electrodes may be located on the distal tip together with a plurality of electrically isolated electrode terminals. The proximal return electrode may or may not be employed in these embodiments. For example, if it is desired to maintain the current flux lines around the distal tip of the probe, the proximal return electrode will not be desired.

What is claimed is:

1. A method for removing material from cardiac tissue comprising:

positioning an electrode terminal in contact with or in close proximity to material attached to cardiac tissue; and applying high frequency voltage to the electrode terminal, the high frequency voltage being sufficient to remove at least a portion of the material from the cardiac tissue.

2. The method of claim 1 wherein the material comprises a calcified deposit.

3. The method of claim 1 wherein the cardiac tissue comprises a heart valve, wherein the material is removed while substantially maintaining the elasticity of the heart valve.

4. The method of claim 1 further comprising removing material from cusps of heart valve leaflets.

5. The method of claim 1 wherein the cardiac tissue comprises commissures of heart valve leaflets, the method further comprising forming an opening in the commissures to enlarge the opening of the heart valve.

6. The method of claim 1 wherein the cardiac tissue comprises an annulus of a heart valve, the method further comprising removing the heart valve from the patient's body.

7. The method of claim 1 further comprising applying sufficient high frequency voltage to the electrode terminal to sculpt the cardiac tissue by removing a portion of the cardiac tissue.

8. The method of claim 1 further comprising volumetrically removing the material from the cardiac tissue in situ while minimizing damage to the cardiac tissue.

9. The method of claim 1 wherein the positioning step comprises advancing an electrosurgical instrument through a percutaneous penetration in the patient's chest.

10. The method of claim 1 wherein the positioning step comprises advancing an electrosurgical catheter transluminally into the patient's heart.

11. The method of claim 1 wherein the positioning step comprises introducing an electrosurgical instrument through an opening in the patient's chest.

12. The method of claim 1 further comprising an electrode array including a plurality of electrically isolated electrode terminals.

13. The method of claim 1 wherein the electrode terminal comprises a single electrode at or near a distal end of an electrosurgical instrument.

14. The method of claim 1 further comprising applying a high frequency voltage difference between the electrode terminal and a return electrode located on an external surface of the patient's body.

15. The method of claim 1 further comprising applying a high frequency voltage difference between the electrode terminal and a return electrode, wherein the return electrode and the electrode terminal are both located on an electrosurgical instrument.

16. The method of claim 1 further comprising positioning the electrode terminal within electrically conductive fluid.

17. The method of claim 16 further comprising delivering the electrically conductive fluid to the electrode terminal to substantially surround the electrode terminal with the electrically conductive fluid.

18. The method of claim 15 further comprising positioning the electrode terminal and the return electrode within electrically conductive fluid to generate a current flow path between the return electrode and the electrode terminal.

19. The method of claim 12 further comprising independently controlling current flow from at least two of the electrode terminals based on impedance between the electrode terminal and a return electrode.

20. The method of claim 16 wherein the electrically conductive fluid is isotonic saline.

21. The method of claim 16 further comprising applying sufficient voltage to the electrode terminal in the presence of the electrically conducting fluid to vaporize at least a portion of the fluid between the electrode terminal and the tissue structure.

22. The method of claim 21 further comprising accelerating charged particles from the vaporized fluid to the tissue structure to cause dissociation of the molecular bonds within the tissue structure.

23. A method as in claim 21 further comprising vaporizing said material to prevent formation of material fragments.

24. A method for removing calcified deposits from a heart valve comprising applying sufficient high frequency electrical energy to calcified deposits on a heart valve to remove said calcified deposits without removing adjacent portions of the heart valve.

25. A method for removing calcified deposits from a heart valve comprising applying sufficient high frequency electrical energy to calcified deposits on a heart valve to remove said calcified deposits while substantially maintaining the elasticity and structure of the heart valve.

* * * * *